(12) United States Patent
Shelton, IV et al.

(10) Patent No.: US 11,992,209 B2
(45) Date of Patent: May 28, 2024

(54) MULTI-THRESHOLD MOTOR CONTROL ALGORITHM FOR POWERED SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Nicholas J. Ross, Franklin, OH (US); Matthew D. Cowperthwait, Cincinnati, OH (US); Curtis A. Maples, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 83 days.

(21) Appl. No.: 17/402,675

(22) Filed: Aug. 16, 2021

(65) Prior Publication Data
US 2023/0051271 A1  Feb. 16, 2023

(51) Int. Cl.
*A61B 17/068* (2006.01)
*A61B 17/072* (2006.01)
(Continued)

(52) U.S. Cl.
CPC ........ *A61B 17/0686* (2013.01); *A61B 17/072* (2013.01); *A61B 34/30* (2016.02);
(Continued)

(58) Field of Classification Search
CPC ... A61B 17/0686; A61B 34/30; A61B 17/072; A61B 2017/0039; A61B 2017/0084; A61B 2017/07257
(Continued)

(56) References Cited

U.S. PATENT DOCUMENTS

| 5,129,570 A | 7/1992 | Schulze et al. |
| 7,404,508 B2 | 7/2008 | Smith et al. |

(Continued)

FOREIGN PATENT DOCUMENTS

| WO | WO 2015/153642 A1 | 10/2015 |
| WO | WO 2017/083125 A1 | 5/2017 |

(Continued)

OTHER PUBLICATIONS

U.S. Appl. No. 17/402,679.
(Continued)

*Primary Examiner* — Robert F Long
*Assistant Examiner* — Xavier A Madison
(74) *Attorney, Agent, or Firm* — Frost Brown Todd LLP

(57) ABSTRACT

A surgical instrument includes a shaft assembly, an end effector, a driving assembly, at least one motor, and a motor controller. The at least one motor is configured to actuate the driving assembly to deploy staples. The motor controller is in communication with the motor. The motor controller is configured to determine whether values of first and second trigger variables exceed predetermined thresholds. The motor controller is configured to modify at least one motor control parameter in response to determining that the values of the first and second trigger variables exceed the predetermined thresholds. The motor control parameters include a motion profile instituted by the motor controller for the motor, a waiting period during which power to the motor is reduced or stopped, or the predetermined threshold relating to current or force for proximal retraction to be different from the predetermined threshold relating to current or force for distal advancement.

20 Claims, 20 Drawing Sheets

(51) Int. Cl.
   *A61B 34/30* (2016.01)
   *A61B 17/00* (2006.01)
(52) U.S. Cl.
   CPC .............. *A61B 2017/00039* (2013.01); *A61B 2017/00084* (2013.01); *A61B 2017/07257* (2013.01)
(58) Field of Classification Search
   USPC .......................................... 227/175.1–182.1
   See application file for complete search history.

(56) References Cited

U.S. PATENT DOCUMENTS

| | | |
|---|---|---|
| 7,434,715 B2 | 10/2008 | Shelton, IV et al. |
| 7,721,930 B2 | 5/2010 | McKenna et al. |
| 7,810,692 B2 | 10/2010 | Hall et al. |
| 7,832,408 B2 | 11/2010 | Shelton, IV et al. |
| 7,845,537 B2 | 12/2010 | Shelton, IV et al. |
| 8,083,120 B2 | 12/2011 | Shelton, IV et al. |
| 8,210,411 B2 | 7/2012 | Yates et al. |
| 8,408,439 B2 * | 4/2013 | Huang ............. A61B 17/07207 227/181.1 |
| 8,453,914 B2 | 6/2013 | Laurent et al. |
| 8,708,213 B2 | 4/2014 | Shelton, IV et al. |
| 9,060,770 B2 | 6/2015 | Shelton, IV et al. |
| 9,186,142 B2 | 11/2015 | Fanelli et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,487 B2 | 12/2017 | Dachs, II |
| 10,011,018 B2 | 7/2018 | McGrogan et al. |
| 10,092,292 B2 | 10/2018 | Boudreaux et al. |
| 10,307,170 B2 | 6/2019 | Parfett et al. |
| 10,485,621 B2 | 11/2019 | Morrissette et al. |
| 10,537,400 B2 | 1/2020 | Dachs, II et al. |
| 10,610,313 B2 | 4/2020 | Bailey et al. |
| 10,667,809 B2 | 6/2020 | Bakos et al. |
| 10,806,530 B2 | 10/2020 | Liao et al. |
| 10,863,988 B2 | 12/2020 | Patel et al. |
| 11,020,138 B2 | 6/2021 | Ragosta |
| 11,026,755 B2 | 6/2021 | Weir et al. |
| 11,076,926 B2 | 8/2021 | Ragosta et al. |
| 11,147,552 B2 | 10/2021 | Burbank et al. |
| 11,166,773 B2 | 11/2021 | Ragosta et al. |
| 11,234,700 B2 | 2/2022 | Ragosta et al. |
| 11,259,884 B2 | 3/2022 | Burbank |
| 2006/0185682 A1 | 8/2006 | Marczyk |
| 2012/0209314 A1 | 8/2012 | Weir et al. |
| 2015/0297228 A1 | 10/2015 | Huitema et al. |
| 2016/0361126 A1 | 12/2016 | Schena et al. |
| 2017/0020617 A1 | 1/2017 | Weir et al. |
| 2017/0265865 A1 | 9/2017 | Burbank |
| 2017/0265954 A1 | 9/2017 | Burbank et al. |
| 2017/0333037 A1 | 11/2017 | Wellman et al. |
| 2018/0168756 A1 | 6/2018 | Liao et al. |
| 2018/0271608 A1 | 9/2018 | Ragosta et al. |
| 2018/0310935 A1 | 11/2018 | Wixey |
| 2018/0325517 A1 * | 11/2018 | Wingardner ..... A61B 17/07207 |
| 2018/0325606 A1 | 11/2018 | Weir et al. |
| 2018/0344419 A1 | 12/2018 | Dachs, II et al. |
| 2018/0360446 A1 * | 12/2018 | Shelton, IV ........ A61B 17/1114 |
| 2019/0038371 A1 | 2/2019 | Wixey et al. |
| 2019/0059889 A1 | 2/2019 | Shelton, IV et al. |
| 2019/0076142 A1 | 3/2019 | Wixey |
| 2019/0076143 A1 | 3/2019 | Smith |
| 2019/0167266 A1 | 6/2019 | Patel et al. |
| 2019/0200989 A1 | 7/2019 | Burbank et al. |
| 2019/0201023 A1 | 7/2019 | Shelton, IV et al. |
| 2019/0201046 A1 | 7/2019 | Shelton, IV et al. |
| 2019/0239967 A1 | 8/2019 | Ragosta et al. |
| 2019/0262088 A1 | 8/2019 | Burbank |
| 2020/0138529 A1 | 5/2020 | Ragosta et al. |
| 2020/0397430 A1 | 12/2020 | Patel et al. |
| 2020/0405301 A1 | 12/2020 | Shelton, IV et al. |
| 2020/0405403 A1 | 12/2020 | Shelton, IV et al. |
| 2021/0393340 A1 | 12/2021 | Beckman et al. |
| 2021/0401433 A1 | 12/2021 | Freidel et al. |

FOREIGN PATENT DOCUMENTS

| | | |
|---|---|---|
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/088,941, entitled "Surgical Stapler End Effector Sled Having Cartridge Wall Support Feature," filed Nov. 4, 2020.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
U.S. Appl. No. 17/402,674.
U.S. Appl. No. 17/402,677.
U.S. Appl. No. 17/402,695.
U.S. Appl. No. 17/402,701.
U.S. Appl. No. 17/402,703.
U.S. Appl. No. 17/402,720.
U.S. Appl. No. 17/402,732.
U.S. Appl. No. 17/402,738.
U.S. Appl. No. 17/402,744.
U.S. Appl. No. 17/402,749.
U.S. Appl. No. 17/402,759.
U.S. Pat. No. 11,779,332.
International Search Report and Written Opinion dated Dec. 12, 2022 for Application No. PCT/IB2022/057611, 16 pgs.

* cited by examiner

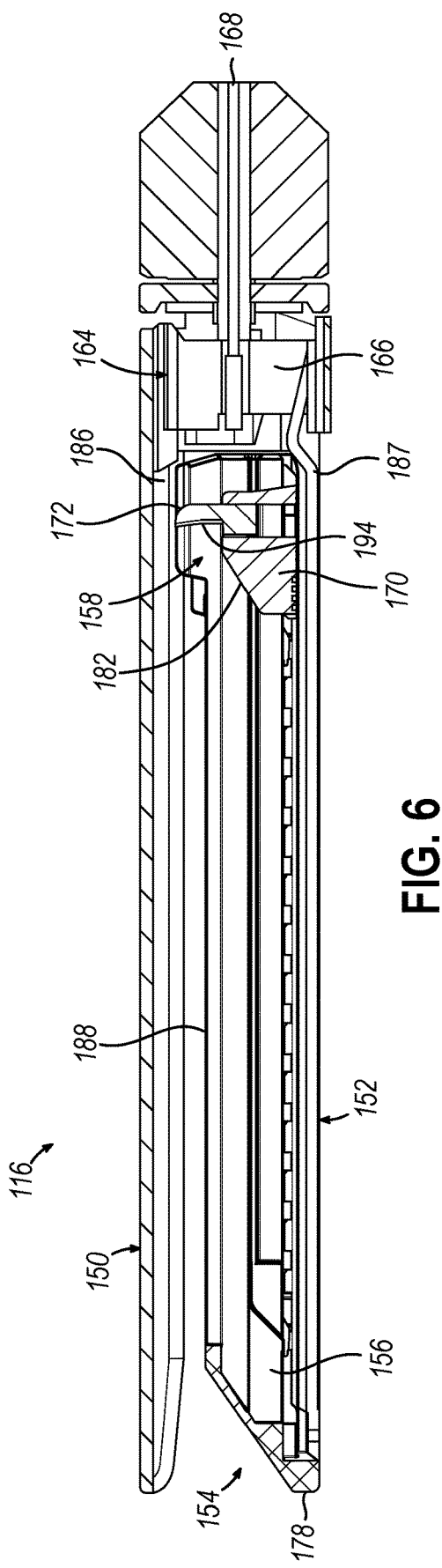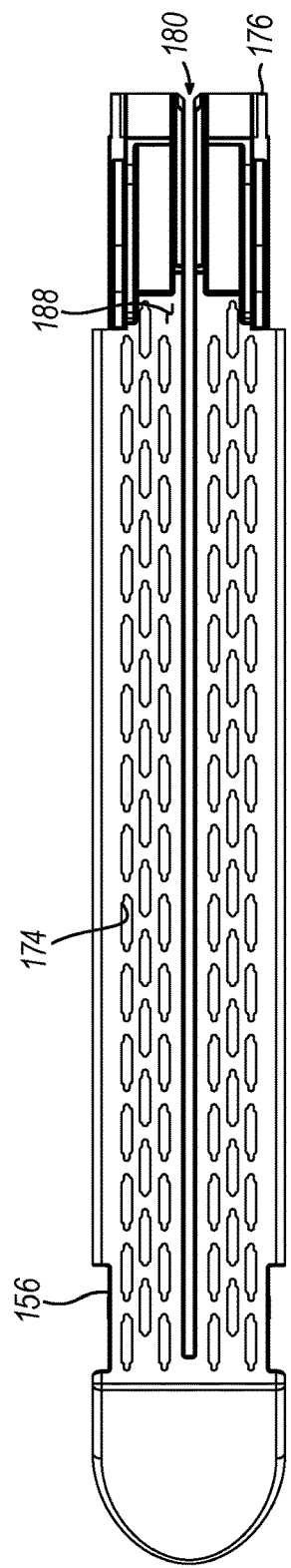

MULTI-THRESHOLD MOTOR CONTROL ALGORITHM FOR POWERED SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side cross-sectional view of the end effector of FIG. 4, where the end effector includes a staple cartridge;

FIG. 7 depicts a top view of a deck of the staple cartridge of FIG. 6;

Figure 1:
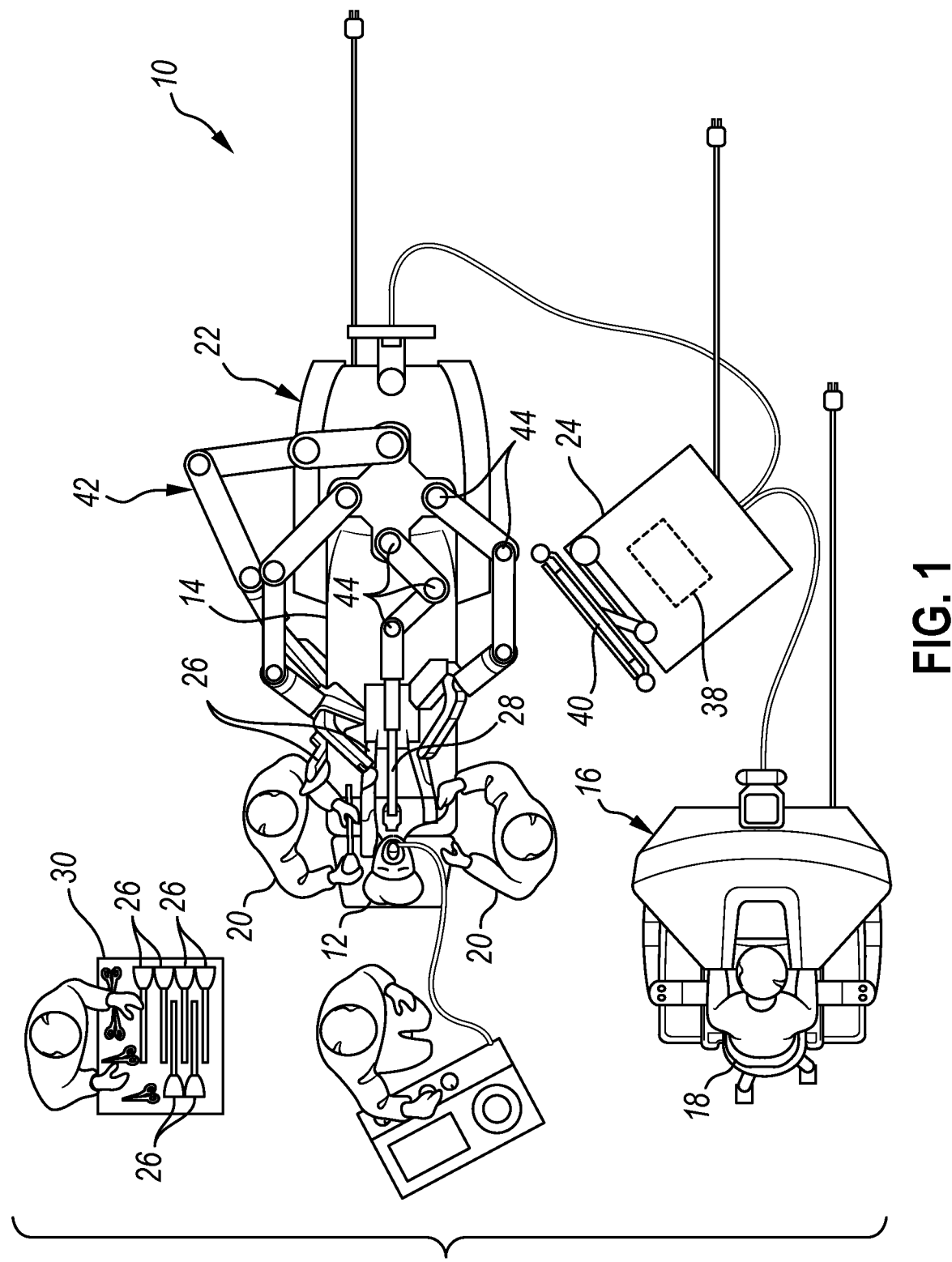
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. EXEMPLARY ROBOTIC SURGICAL SYSTEM

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018, issued as U.S. Pat. No. 11,076,926 on Aug. 3, 2021; U.S. Pub. No. 2018/0325606, entitled "Systems and Methods for Operating an End Effector," published Nov. 15, 2018, issued as U.S. Pat. No. 11,026,755 on Jun. 8, 2021; U.S. Pub. No. 2019/0200989, entitled "Stapler Reload Detection and Identification," published Jul. 4, 2019, issued as U.S. Pat. No. 11,364,029 on Jun. 21, 2022; U.S. Pub. No. 2019/0239967, entitled "Stapler Beam Architecture," published Aug. 8, 2019, issued as U.S. Pat. No. 11,166,773 on Nov. 9, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2019/0239877, entitled "Wrist Architecture," published Aug. 8, 2019, issued as U.S. Pat. No. 11,234,700 on Feb. 1, 2022; U.S. Pub. No. 2019/0201150, entitled "Push-Pull Surgical Instrument End Effector Actuation Using Flexible Tension Member," published Jul. 4, 2019, issued as U.S. Pat. No. 11,020,138 on Jun. 1, 2021; U.S. Pub. No. 2019/0282233, entitled "Stapler Cartridge With an Integral Knife," published Sep. 19, 2019, issued as U.S. Pat. No. 11,147,552 on Oct. 19, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2020/0138529, entitled "Locking System for Medical Device Drive System," published May 7, 2020, issued as U.S. Pat. No. 11,633,239 on Apr. 25, 2023; and/or U.S. Pub. No. 2020/0397430, entitled "Surgical Instrument With Lockout Mechanism," published Dec. 24, 2020, issued as U.S. Pat. No. 11,439,390 on Sep. 13, 2022. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
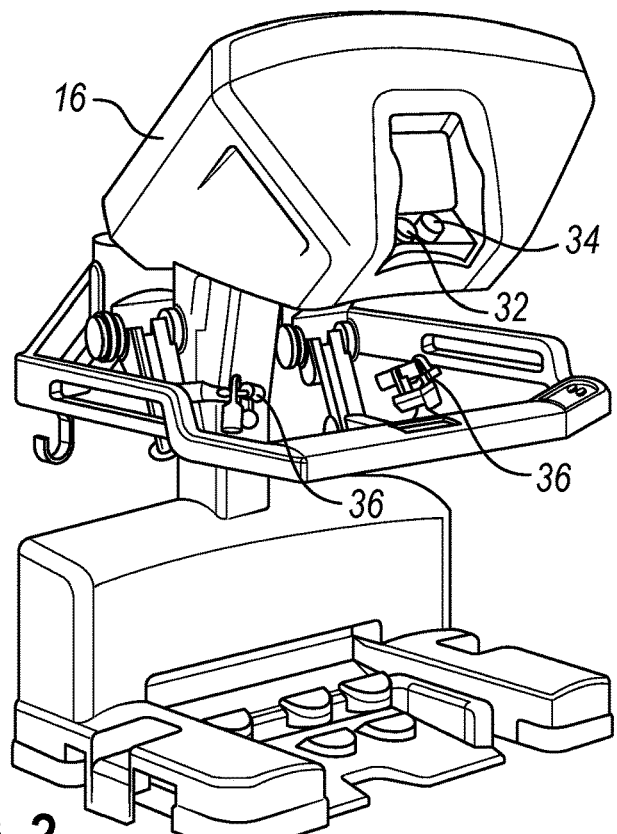
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
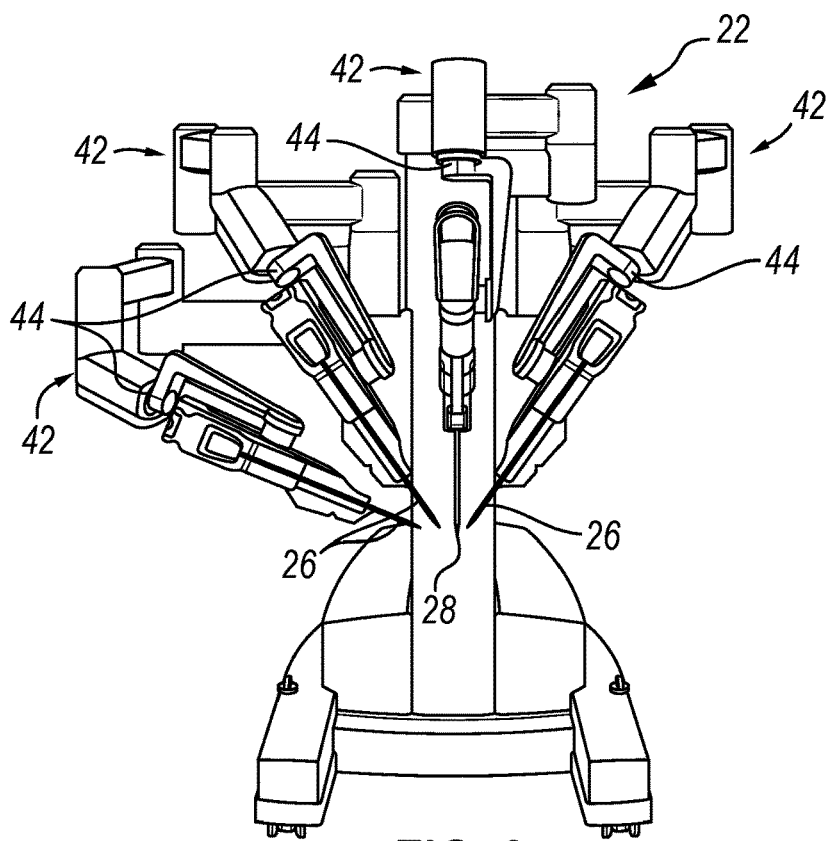
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
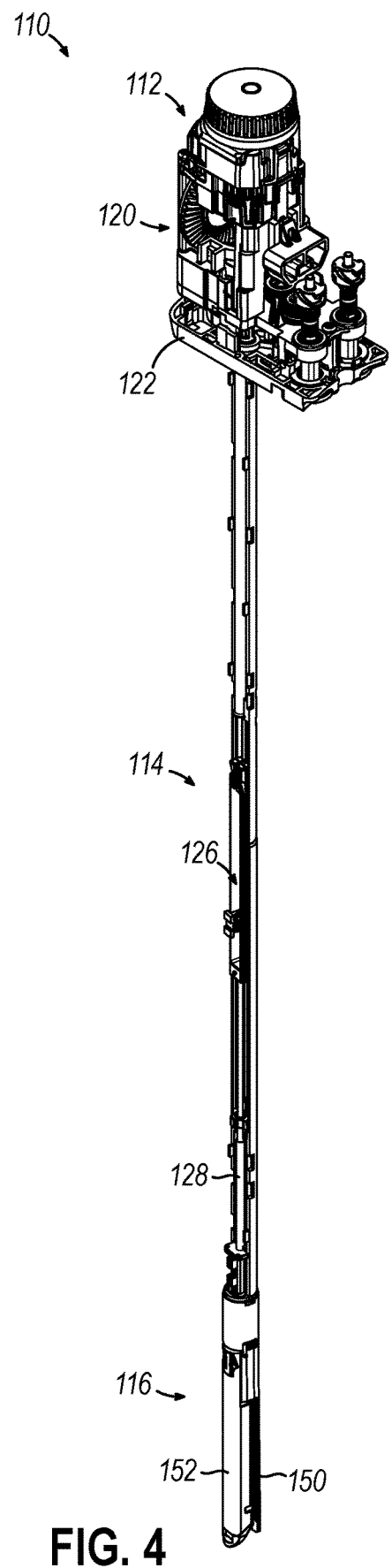
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
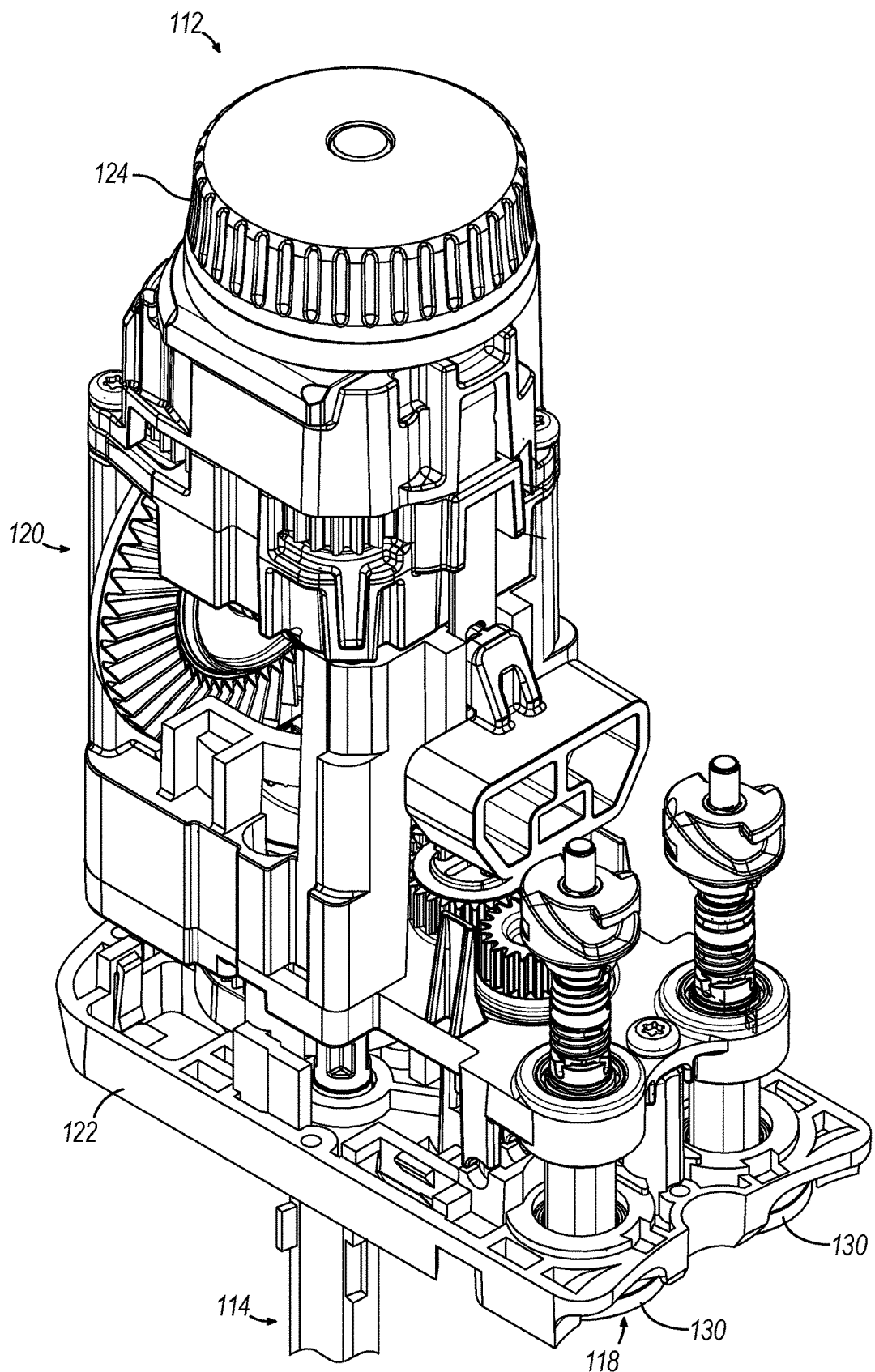
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
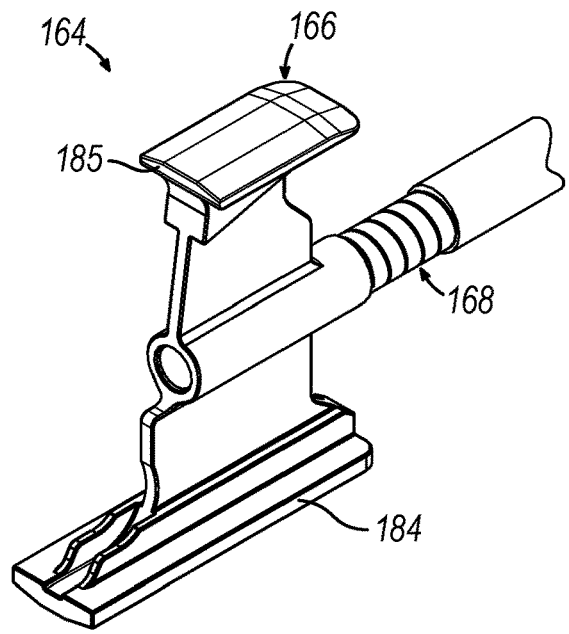
FIG. 8 depicts a driving assembly configured for use with the staple cartridge of FIG. 7.
Figure 9:
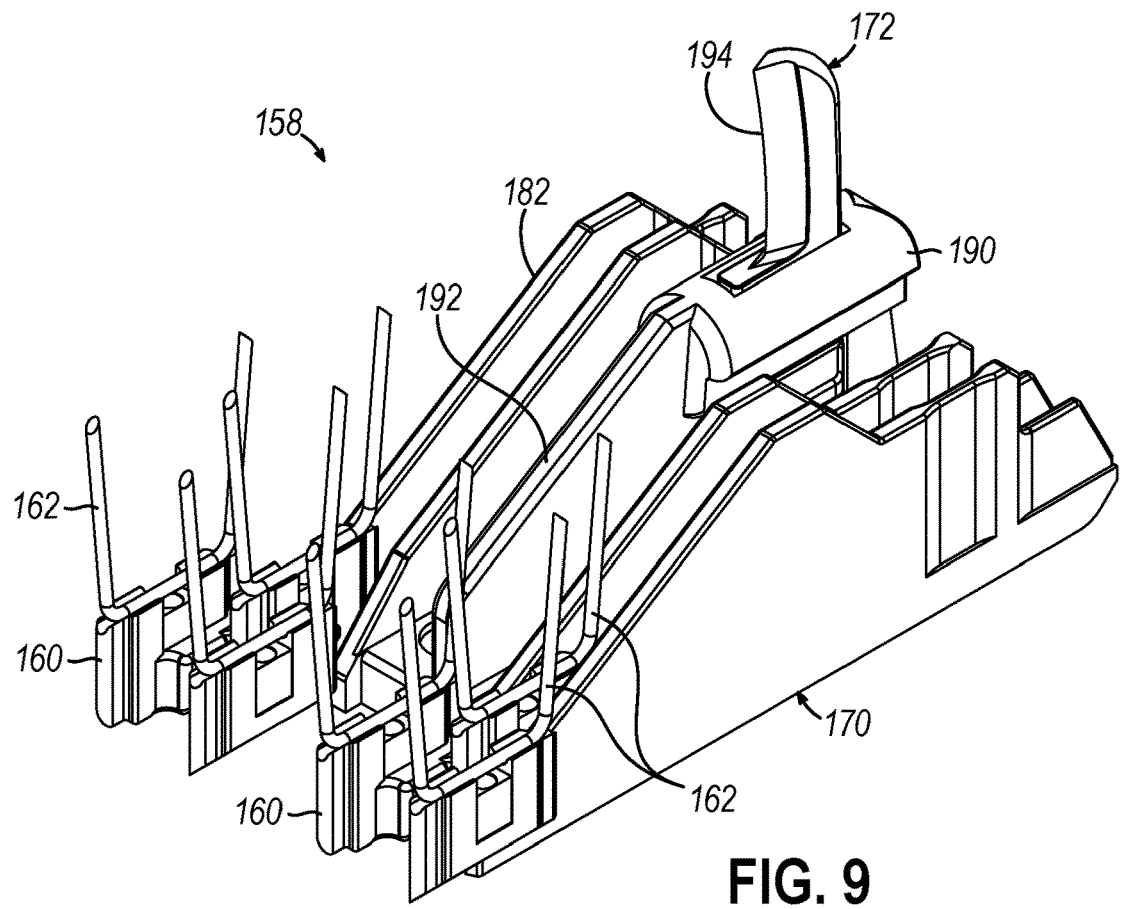
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

FIG. 7 shows atop view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled (170) contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
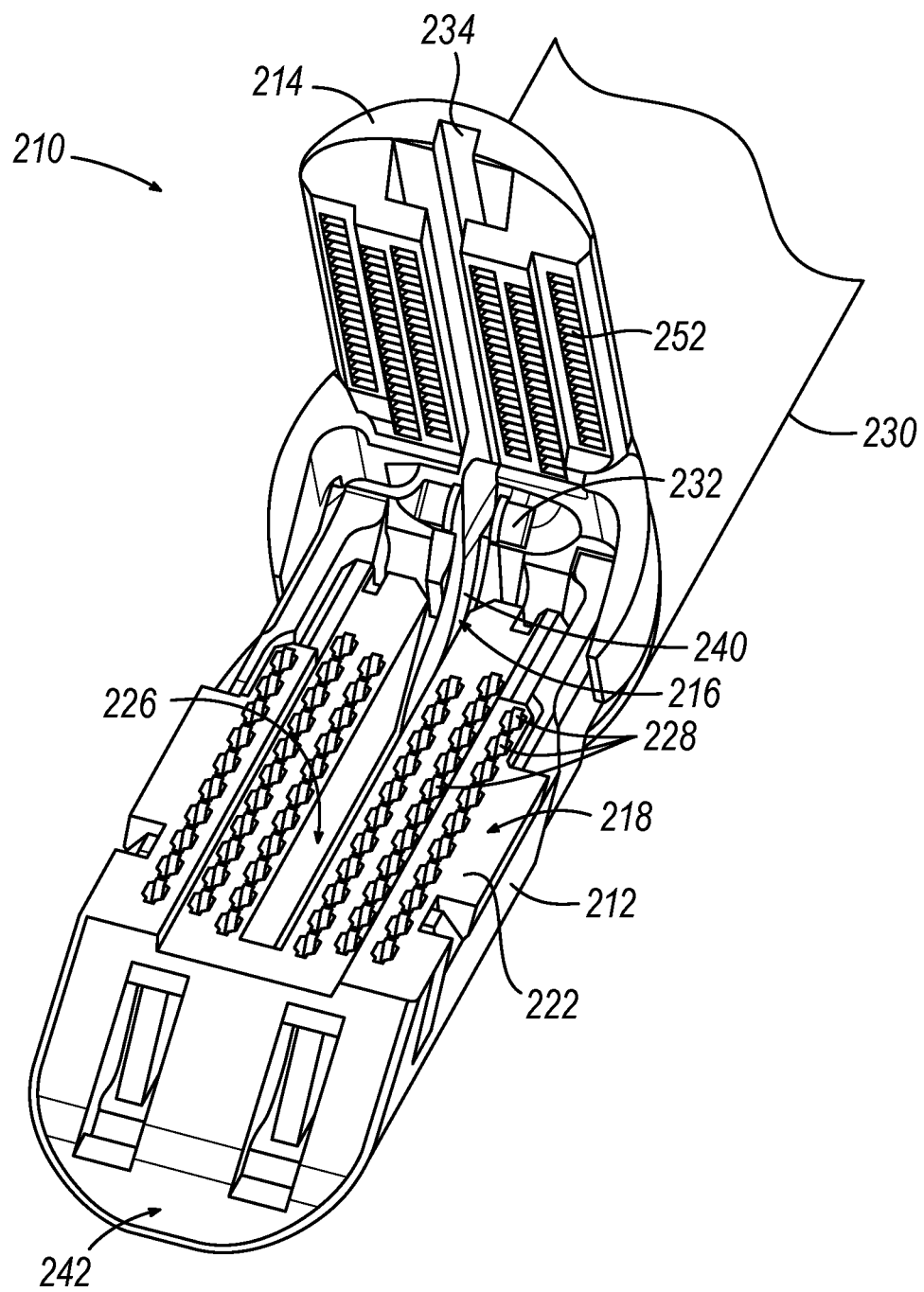
FIG. 10 depicts a second exemplary end effector that may be configured for use with the robotic surgical system of FIG. 1.
Figure 11:
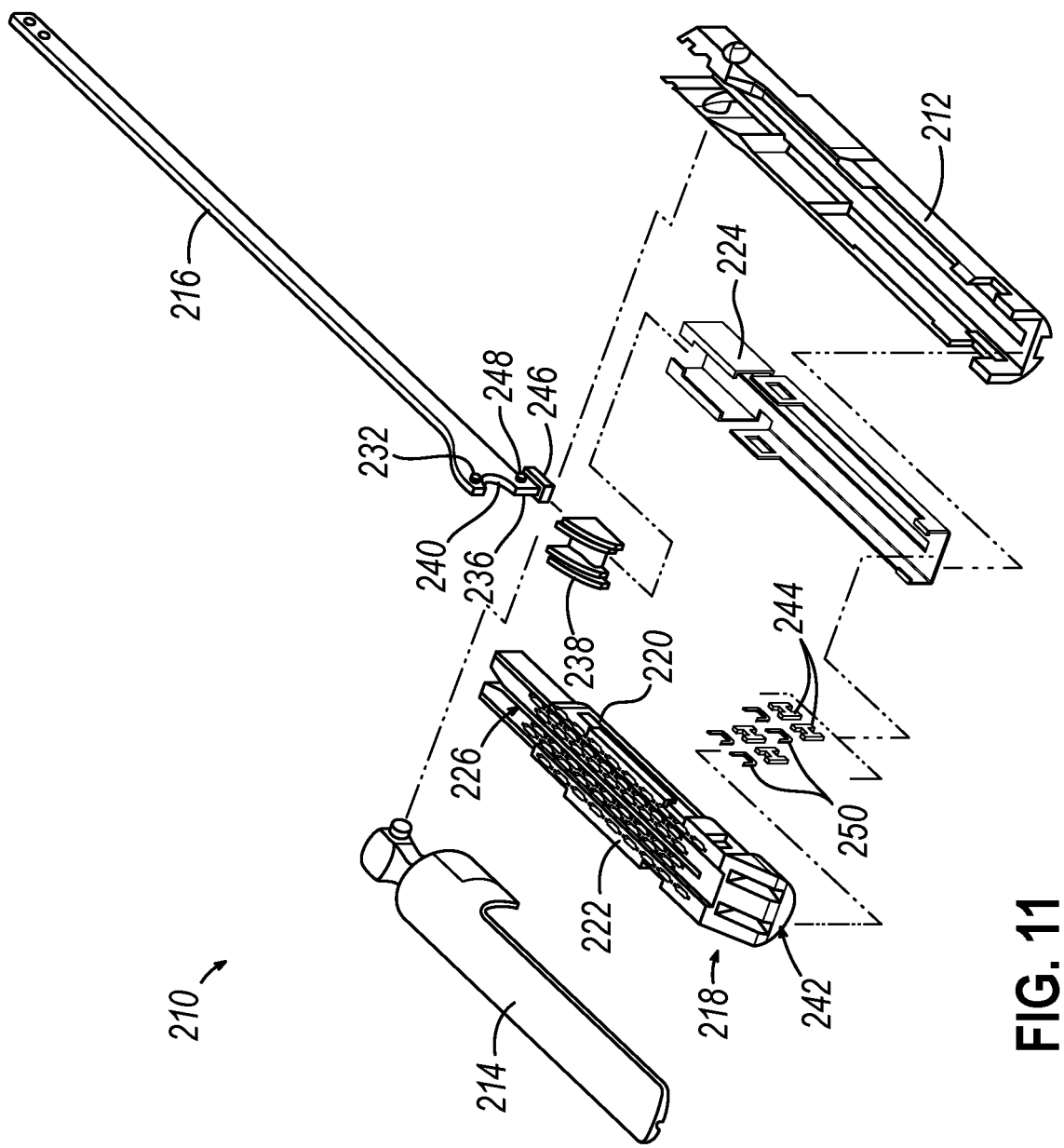
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin (232) of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021, the disclosure of which is hereby incorporated by reference herein in its entirety.

It will be appreciated that any one or more of the teachings described below may be combined with any one or more of the teachings described above in connection with FIGS. 1-11.

II. EXEMPLARY MULTI-THRESHOLD MOTOR CONTROL ALGORITHM FOR SURGICAL STAPLER

A. System Overview

It may be desirable to improve motor control of one or more motors associated with robotic arm (42) and/or surgical instrument (26) described above to better compensate for a particular state of the motor and thereby improve performance of surgical instrument (26) during a surgical procedure. For example, it may be beneficial to improve motor efficiency and transitions from a static state to n active state, as well as to account for variable manufacturing tolerances and/or differing powering capacities of the motor(s). The exemplary methods and configurations described below provide such enhanced capabilities.

Figure 12:
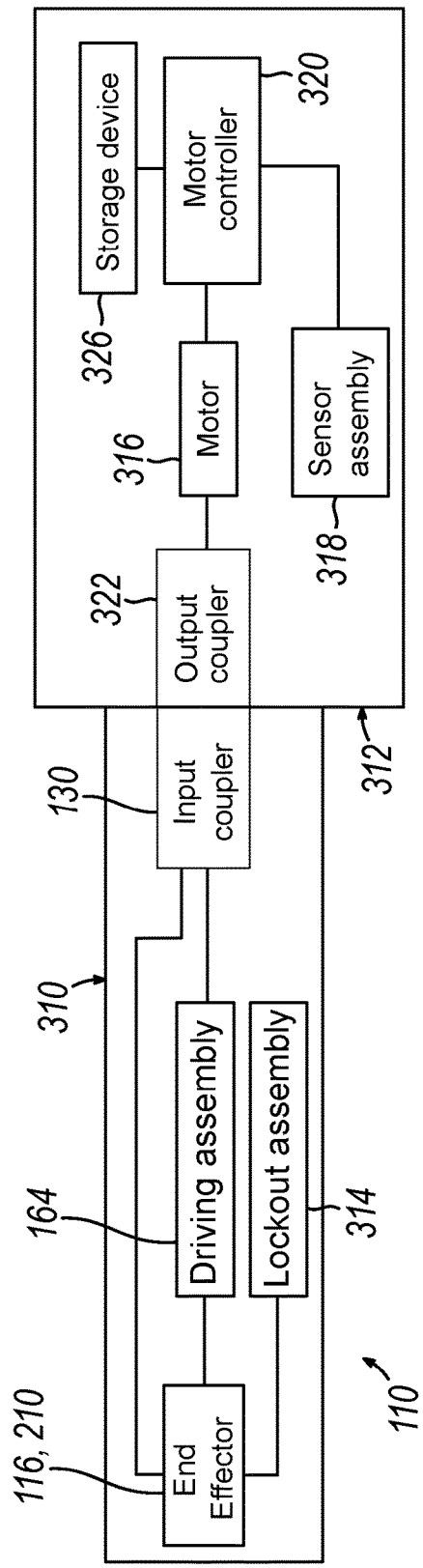
FIG. 12 depicts a schematic view of another exemplary robotic surgical system similar to the robotic surgical system of FIG. 1.

FIG. 12 shows another exemplary robotic surgical system (310) that includes a robotic arm (312) and a surgical instrument, shown in the form of surgical instrument (110) which is configured to removably couple with robotic arm (312). Robotic surgical system (310) is similar to robotic surgical system (10) with differences described below. For example, robotic arm (312) may be similar to robotic arm (42) described above with reference to FIGS. 1-4. Robotic arm (312) may suitably interact with robotic surgical system (310) such that a medical professional operator may utilize robotic surgical system (310) to control instrument (110) via robotic arm (312), input control devices (36) of surgeon's console (16), and any other suitable intermediate components as would be apparent to one skilled in the art in view of the teachings described herein.

As previously described with reference to FIGS. 4-10, surgical instrument (110) includes shaft assembly (114), driving assembly (164), and end effector (116, 210). Driving assembly (164) may extend through at least a portion of shaft assembly (114) and end effector (116, 210). Driving assembly (164) is operable to staple and cut tissue based on instruction from motor controller (320). End effector (116, 210) includes first and second jaws (150, 152, 212, 214). At least one of first or second jaws (150, 152, 212, 214) is configured to pivot relative to the other of first or second jaws (150, 152, 212, 214). End effector (116, 210) is operatively coupled with shaft assembly (114). First jaw (150, 212) includes an anvil, and second jaw (152, 214) is configured to receive staple cartridge (154, 218) that includes staples (250). Lockout assembly (314) may be moved between a lockout configuration and a non-lockout configuration. The lockout configuration prevents actuation of firing assembly (158). In the lockout configuration, the complete firing of end effectors (116, 210) is prevented. Conversely, the non-lockout configuration allows for actuation of firing assembly (158).

Robotic arm (312) includes at least one motor (316), a sensor assembly (318), and a motor controller (320). One or more output couplers (322) of robotic arm (312) are configured to selectively couple with at least one or more input couplers (130) of surgical instrument (110). Input coupler (130) is configured to interface with and be driven by output coupler (322) of robotic arm (312). Output coupler (322) and input coupler (130) may include any suitable components as would be apparent to one skilled in the art in view of the teachings herein. Motor controller (320) may be in communication with input control devices (36) of surgeon's console (16).

Any suitable number of input couplers (130) and any suitable number of output couplers (322) may be utilized as would be apparent to one skilled in the art in view of the teachings herein. While not shown, a first output coupler (322) may couple with a first input coupler (130) and a second output coupler (not shown) may couple with a second input coupler (not shown). For example, the second input coupler may be controlled by a second motor to perform separate functions. In instances where end effector (210) is operatively attached to the distal end of shaft assembly (114), motor (316) and the respective output coupler (322) and input coupler (130) may be utilized to actuate firing beam (216); while second motor (not shown) and the respective output coupler (not shown) and second input coupler (not shown) may be utilized to actuate closure tube (not shown) and closure ring (230).

Motor (316) is configured to actuate driving assembly (164) to deploy staples from staple cartridge (154, 218). Motor (316) is configured to drive firing assembly (158) within end effector (116, 210) to advance knife through end effector (116, 210) or fire a plurality of staples (250) out of staple cartridge (154, 218). Motor controller (320) is in communication with motor (316). Sensor assembly (318) is configured to sense values of interrelated trigger related to operation of motor (316). As shown, sensor assembly (318) is disposed within robotic arm (312); however, it is envisioned that sensor assembly (318) may be positioned in a variety of locations that are suitable to instruct the operation of motor (316). For example, sensor assembly may be disposed within surgical instrument (110) (e.g., in or adjacent to end effector (116, 210)). Sensor assembly (318) may include one or more of a force sensor, a current sensor, a temperature sensor, or a position sensor. Data obtained from sensor assembly (318) may be stored on storage device (326) for later access by motor controller (320).

Motor controller (320) may also be in communication with storage device (326) such that motor controller (320) may communicate data to storage device (326), and such that motor controller (320) may access and utilize data stored on storage device (326). Motor controller (320) and storage device (326) may contain any suitable number of components as would be apparent to one skilled in the art in view of the teachings herein. Motor controller (320) may utilize data contained in storage device (326) in order to establish operational parameters for robotic arm (342) while controlling a specific instrument (110).

Motor controller (320) may recall and utilize data stored on storage device (326) related to specific instruments (110) when that specific instrument (110) is coupled to robotic arm (312) for exemplary use in accordance with the description herein. For example, storage device (326) may be configured to store predetermined thresholds (e.g., force thresholds, temperature thresholds, voltage thresholds) pertaining to the specific instrument (110) in accordance with the teachings herein. Storage device (326) may be configured to store information related to a specific instrument (110), such as any suitable data accumulated during exemplary use of a specific instrument (110) as would be apparent to one skilled in the art in view of the teachings herein. In some instances, a specific instrument (110) may have an identifiable chip or other electronic device that notifies motor controller (320) of the specific instrument (110) that is coupled with robotic arm (342), therefore allowing motor controller (320) to track the specific instrument (110) and data stored on storage device (326) related to the specific instrument (110). In some instances, the specific instrument (110) may include its own storage device (326) that establishes communication with motor controller (320) when instrument (110) is initially coupled with robotic arm (312). In such instances, information regarding prior use of a specific instrument (110) may be stored on that instrument's specific storage device and accessed by motor controller (320) when the specific instrument (110) is coupled to robotic arm (312).

While in the current example, storage device (326) is housed within robotic arm (312), storage device (326) may be associated with any suitable component as would be apparent to one skilled in the art in view of the teachings herein. For example, storage device (326) may be housed within instrument (110) such that storage device (326) may selectively establish communication with motor controller (320) while instrument (110) is coupled to robotic arm (312). As another example, storage device (326) may be associated with surgeon's console (16). In other instances, multiple storage devices (326) may be utilized, each associated with various components, such that each storage device (326) stores data related to the respective specific component.

B. Exemplary Method

Figure 13:
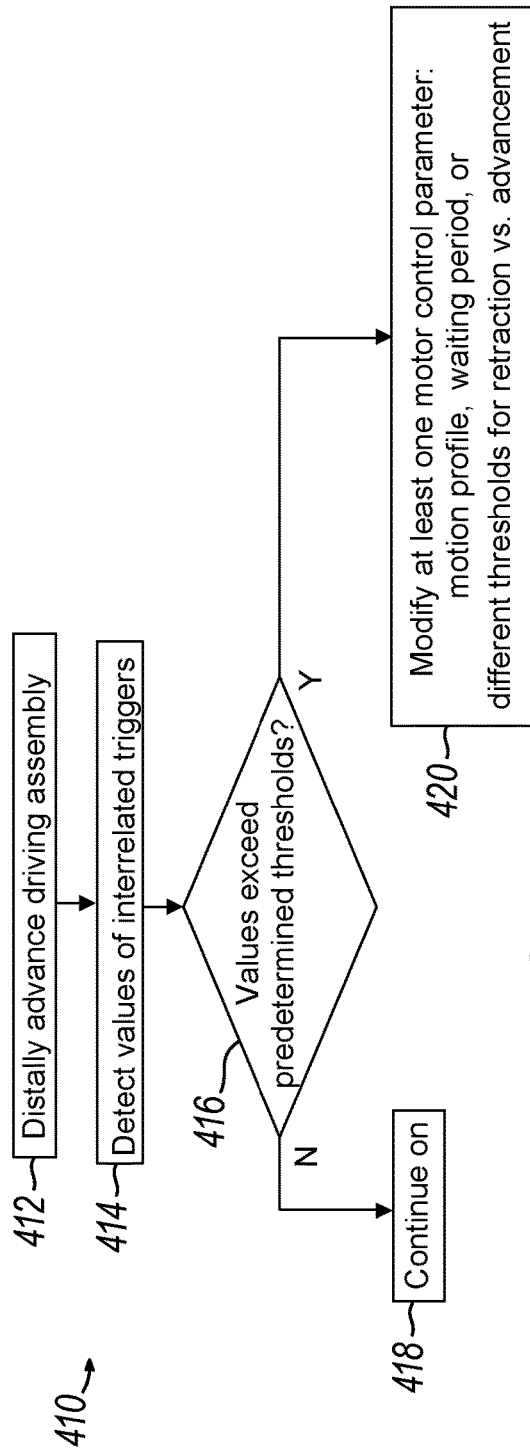
FIG. 13 depicts a block diagram of a first exemplary motor control algorithm that may be used by the robotic arm and surgical instrument shown in FIG. 12.

As described with reference to FIG. 13, method (410) includes exemplary steps (412, 414, 416, 418, 420). At step (412), motor controller (320) may activate motor (316) to distally advance driving assembly (164) into contact with firing assembly (158). At step (414), interrelated triggers may be measured or otherwise detected. In some versions, the values of the interrelated triggers may be detected using sensor assembly (318). The interrelated triggers affect at least one motor control parameter.

At step (416), motor controller (320) may determine whether the measured values of interrelated triggers exceed predetermined thresholds. For example, the predetermined thresholds may include a measured firing motor force that exceeds a maximum firing motor force threshold of motor (316), a measured temperature that exceeds a maximum temperature threshold of motor (316), a measured current that exceeds a maximum current threshold of motor (316) and/or a measured distance exceeds the lockout value (indicating lockout assembly (314) is in the non-lockout configuration). As will be described in greater detail below with reference to FIGS. 14-22, the interrelated triggers may include firing motor force, firing motor current, or firing motor temperature, and/or duty cycle. It is envisioned that any one of the triggers referenced in FIGS. 14-22 may be used in combination with another one or more triggers referenced in FIGS. 14-22. Using multiple triggers in combination may provide additional benefits, and may have a cumulative effect that is different than the triggers being assessed and modified separately. In other words, there are cooperative benefits associated with modifying the performance of motor (316) using multiple trigger variables in combination.

At step (418), if the measured values of the interrelated triggers do not exceed the predetermined thresholds, motor controller (320) continues operation according to a predetermined motion profile. However, at step (420), if one or more of the measured values of interrelated triggers do exceed the predetermined thresholds, motor controller (320) may modify at least one motor control parameter of motor (316). Exemplary motor control parameters may include, for example, a motion profile instituted by motor controller (320) using motor (316), awaiting period where power to motor (316) is reduced or stopped, or differing thresholds based on whether driving assembly (164) is distally advancing or proximally retracting. For example, the motor firing current threshold and/or the firing motor force threshold for retraction may be greater than the predetermined threshold for advancement. In some versions, in response to the values exceeding the predetermined thresholds, motor controller (320) is configured to modify two or more motor control parameters. As will be described in greater detail below with reference to FIGS. 14-22, the motor control parameters may cooperate to determine max control motions, waits, or change in operation. The control parameters may include wait time, alternating cycle rate, speed control, or changing the threshold limits. The motion profile may be sustained or intermittent pulse of motor power to change performance of driving assembly (164) (see FIG. 8) or firing beam (216) (see FIG. 11) on end effector (116, 210). In some versions, motor controller (320) is configured to withhold modification of at least one motor control parameter until each of the values of the first and second triggers exceed their respective predetermined thresholds. In some versions, the motor controller (320) is configured to modify one motor control parameter(s) differently in response to each of the values of the first and second interrelated trigger exceeding the predetermined thresholds as compared to a single one of the interrelated triggers exceeding the respective predetermined threshold.

During the firing process (either advancement prior or retraction), driving assembly (164) or firing beam (216) may become undesirably stuck due to frictional binding in a longitudinal position relative to staple cartridge (154, 218) such that driving assembly (164) or firing beam (216) relative to staple cartridge (154, 218) is inhibited beyond a tolerable degree. For example, during proximal retraction of pusher member (166) (see FIG. 8) in accordance with the description herein, flanges (184, 185) may overly engage or dig into portions of staple cartridge (154) and/or jaws (150, 152) defining associated longitudinal slots (186, 187), thereby inhibiting suitable movement due to an undesirable amount of frictional binding. As another example, during distal advancement of firing beam (216), upper pin (232) or firing beam cap (246) (see FIG. 11) may overly engage or dig into portions of staple cartridge (218) defining longitudinal anvil slot (234) or lower surface of lower jaw (212), respectively, thereby inhibiting suitable movement due to an undesirable amount of frictional binding. It is desirable for motor controller (320) to operate motor (316) in a manner that minimized or overcomes these issues.

C. Motor Control Using Algorithmic Bumping

Figure 14:
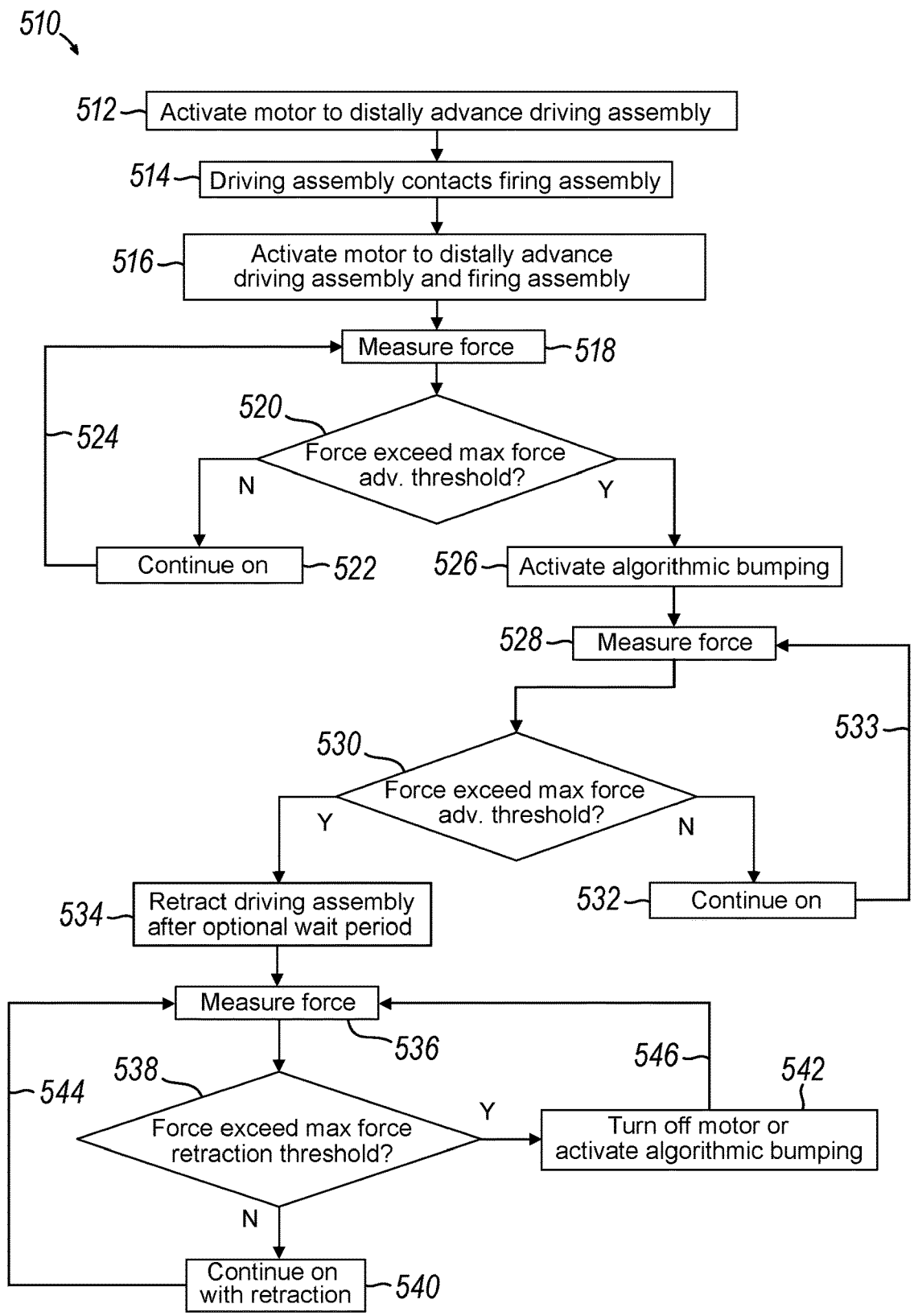
FIG. 14 depicts a block diagram of a second exemplary motor control algorithm that may be used by the robotic arm and surgical instrument shown in FIG. 12.
Figure 15:
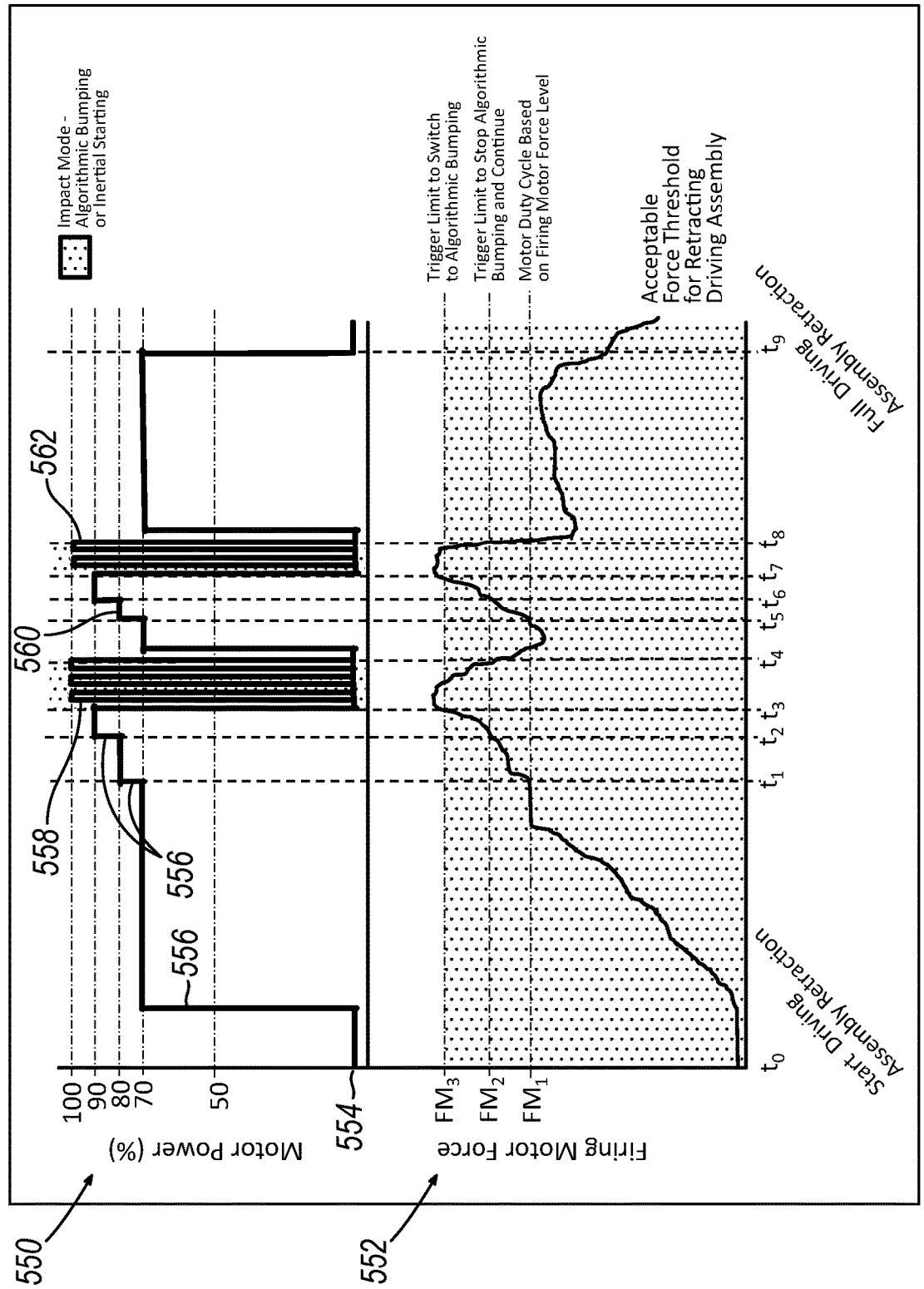
FIG. 15 depicts a multi-axis line graph with plots of motor power and firing motor force with respect to time.

As described with reference to FIG. 14-15, method (510) may include exemplary steps (512, 514, 516, 518, 520, 522, 524, 526, 528, 530, 532, 533, 534, 536, 538, 540, 542, 544, 546). While FIGS. 14-15 are described below with reference to the structures of FIGS. 1-9, method (510) may also be used with the structures of FIGS. 10-11. At step (512), motor controller (320) to activate motor (316) may distally advance driving assembly (164). At step (514), motor controller (320) may activate motor (316) so that driving assembly (164) contacts firing assembly (158). At step (516), motor controller (320) may activate motor (316) to distally advance driving assembly (164) and firing assembly (158). At step (518), firing motor force may be measured. This firing motor force may be measured by motor controller (320) interpreting data produced by motor (316) during operation and/or through the use of a sensor assembly (318) operatively coupled with motor (316) and motor controller (320). At step (520), motor controller (320) may determine whether the measured firing motor force exceeds the maximum advancement firing motor force threshold. Threshold values may be stored in storage device (326) for retrieval by motor controller (320). At step (522), if the measured firing motor force does not exceed the maximum advancement firing motor force threshold using motor controller (320), motor (316) may continue on using a predetermined firing sequence until completion of the firing sequence. At step (524), steps (518, 520, 522) may be repeated as described above (one or more times) to repeatedly determine whether the measured firing motor force exceeds the maximum advancement firing motor force.

At step (526), if the measured firing motor force exceeds the maximum advancement firing motor force threshold as determined by motor controller (320), motor controller (320) may instruct motor (316) to use algorithmic bumping or a soft start. As described below with reference to plot (550) of FIG. 15 showing retraction of driving assembly (164), algorithmic bumping (558, 562) repeatedly provides power to motor (316) then stop power to motor (316). For a soft start, motor controller (320) gradually increases power to motor (316) (e.g., by incrementally stepping up the power to motor (316)). At step (528), firing motor force may be measured, similar to step (518). At step (530), motor controller (320) may determine whether the measured firing motor force exceeds the maximum advancement firing motor force threshold, similar to step (520). At step (532), if the measured firing motor force does not exceed the maximum advancement firing motor force threshold as determined motor controller (320), motor (316) may continue on until completion of the firing sequence. At step (533), steps (528, 530, 532) may be repeated (one or more times) to determine whether the measured firing motor force exceeds the maximum advancement firing motor force.

At step (534), if the measured firing motor force exceeds the maximum advancement firing motor force threshold as determined by motor controller (320), motor controller (320) may instruct motor (316) to retract driving assembly (164) in a proximal direction, which is opposite to the distal direction of advancement. Plots (550, 552) of FIG. 15 show comparisons of motor power (as a percentage of maximum power) and firing motor force during retraction of driving assembly (164). Time (t0) refers to the time when driving assembly (164) starts being retracted, while time (t9) refers to the time when driving assembly (164) is fully retracted.

At step (534), motor (316) optionally pauses or begins retracting driving assembly (164) based on instructions from motor controller (320). For example, at time (t0), shown by line (554) in plot (550), power to motor (316) may be approximately equal to zero to implement an optional waiting period. As shown, motor controller (320) instructs motor (316) to incrementally increase motor power using a soft start (556).

At step (536), firing motor force may be measured, similar to step (518). At step (538), if the measured firing motor force exceeds the maximum retraction firing motor force threshold using motor controller (320), motor controller (320) may instruct motor (316) to turn off or activate algorithmic bumping. It may be desirable to have different values for the maximum retraction firing motor force threshold as compared to the maximum advancement firing motor force threshold. In some versions, the maximum retraction firing motor force threshold exceeds the maximum advancement firing motor force threshold. Algorithmic bumping (also referred to as inertial starting) allows driving assembly (164) to improve the likelihood of moving relative to staple cartridge (154, 218) to overcome the static binding. At step (540), if the measured retraction firing motor force does not exceed the maximum retraction firing motor force threshold using motor controller (320), motor (316) may continue on (illustrated in FIG. 15 at times (t1, t2)) until completion of the retraction sequence. The stippling shaded region depicted of plot (552) of FIG. 15 represents the tolerable firing motor force threshold for retracting driving assembly (164). At step (544), steps (536, 538, 540) may be repeated as described above to repeatedly determine whether the measured firing motor force exceeds the maximum retraction firing motor force.

At step (542), if the measured retraction firing motor force exceeds the maximum retraction firing motor force threshold determined by motor controller (320), motor controller (320) instructs motor (316) to power off or switch to algorithmic bumping (558). As shown at time (t3) of FIG. 15, once firing motor force (FM3) is exceeded in plot (552), motor controller (320) instructs motor (316) to switch to algorithmic bumping (558) in plot (550). The stippling shaded regions depicted of plot (550) of FIG. 15 represents impact modes where algorithmic bumping (558, 562) is implemented to improve the effective firing motor force to provide an alternative to maximum retraction of driving assembly (164). In other words, motor controller (320) is configured to repeatedly start and stop motor (316) until the measured firing motor force is less than firing motor force threshold (FM2) to stop algorithmic bumping (558). To obtain this algorithmic bumping (558), motor controller (320) may modify the motion profile by instructing motor (316) to provide an intermittent pulse of power to alter performance of end effector (116, 210). As shown in FIG. 15, this algorithmic bumping (558) continues until time (t4) where the measured firing motor force no longer exceeds firing motor force (FM2), which acts as the trigger for stopping algorithmic bumping (558). Between time (t4) and time (t7), firing motor force is incrementally increased using a soft start (560) shown in plot (550) of FIG. 15. At time (t7), firing motor force again exceeds firing motor force (FM3), causing a switch to algorithmic bumping (562) similar to algorithmic bumping (558). This algorithmic bumping (662) continues until time (t8) where the measured firing motor force no longer exceeds firing motor force (FM2). At time, time (t9), driving assembly (164) or is fully retracted.

In some versions, motor current may serve as a substitute for firing motor force, such that firing motor current may be a trigger for alternating between the states. Additionally, the firing motor current (and optionally duty cycle) may cooperatively impact the wait period (dwell time) before engaging the second system or re-engaging the first. Duty cycle is the ratio of time a load or circuit is "on" compared to the time the load or circuit is "off". Duty cycle may be expressed as a percentage of time a load or circuit is "on". In other versions, motor (316) is configured to repeatedly start and stop motor (316) if the measured firing motor temperature is less than a maximum firing motor temperature threshold.

D. Motor Control Using Temperature

It may be desirable to prevent overheating of motor (316) by incorporating thermal control with trigger thresholds for adjustments to motor (316). As a result, motor controller (320) is able to mitigate overheat conditions and limit maximum firing motor performance due to heating.

Figure 16:
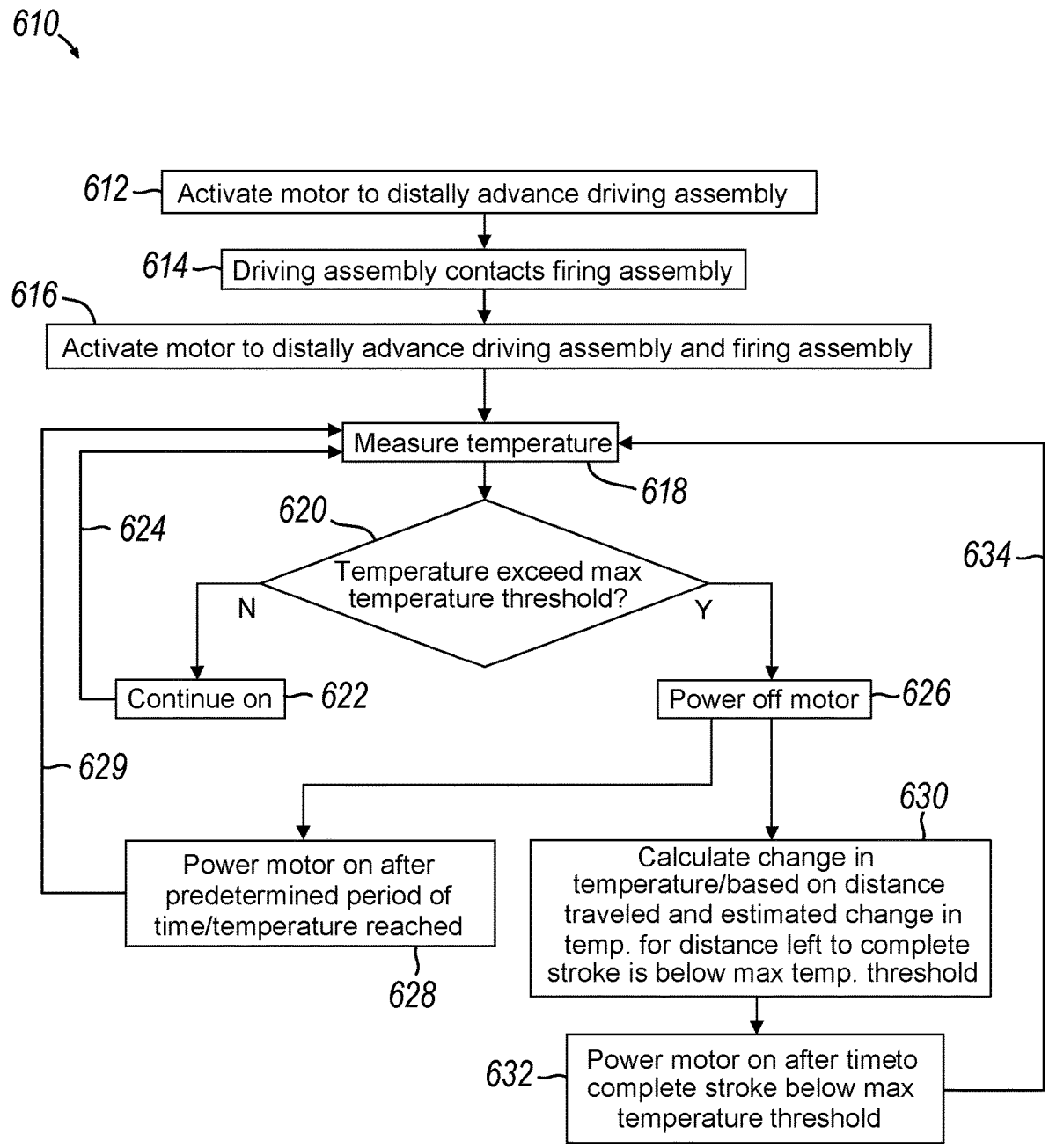
FIG. 16 depicts a block diagram of a third exemplary motor control algorithm that may be used by the robotic arm and surgical instrument shown in FIG. 12.
Figure 17:
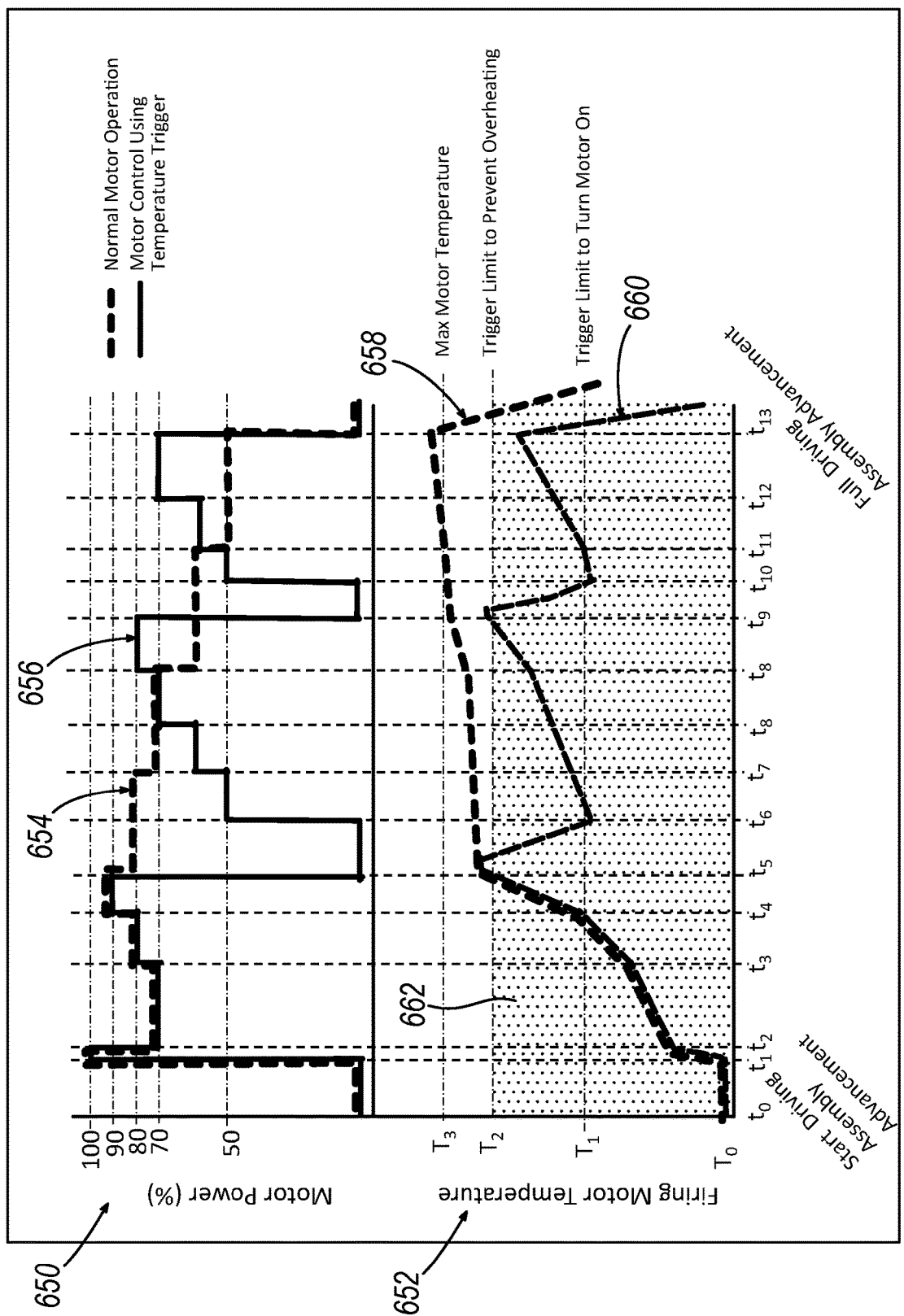
FIG. 17 depicts a multi-axis line graph with plots of motor power and firing motor temperature with respect to time.

As described with reference to FIGS. 16-17, method (610) includes exemplary steps (612, 614, 616, 618, 620, 622, 624, 626, 628, 629, 630, 632, 634) which is described together with plots (650, 652) of FIG. 17. While FIGS. 16-17 are described below with reference to the structures of FIGS. 1-9, method (610) may also be used with the structures of FIGS. 10-11. At step (612), motor controller (320) may activate motor (316) to distally advance driving assembly (164).

Plots (650, 652) of FIG. 17 show comparisons of firing motor power and firing motor temperature during advancement of driving assembly (164). Particularly, plot (650) shows overlying comparisons of firing motor power and respect to time of normal control operation (654) using a dashed line compared to motor control using firing motor temperature triggers (656) using a solid line. Similarly, plot (652) shows overlying comparisons of firing motor temperature and respect to time of normal control operation (658) using a dashed line compared to motor control using firing motor temperature triggers (660) using a solid line. Time (t0) refers to the time when driving assembly (164) starts being advanced distally, while time (t13) refers to the time when driving assembly (164) is fully advanced distally. The stippling shaded region depicted of plot (652) of FIG. 17 represents the tolerable firing motor temperature threshold for driving assembly (164).

At step (614), motor controller (320) may activate motor (316) so that driving assembly (164) contacts firing assembly (158). At step (616), motor controller (320) may activate motor (316) to distally advance driving assembly (164) and firing assembly (158). At step (618), firing motor temperature may be measured. This firing motor temperature may be measured by motor controller (320) interpreting data produced by motor (316) during operation and/or through the use of a sensor assembly (318) operatively coupled with motor (316) and motor controller (320).

At step (620), motor controller (320) may determine whether the measured firing motor temperature exceeds the maximum firing motor temperature threshold. The firing motor temperature threshold may be stored in storage device (326) for retrieval by motor controller (320). At step (622), if the measured firing motor force does not exceed the maximum temperature threshold using motor controller (320), motor (316) may continue on using a predetermined firing sequence until completion of the firing sequence. At step (624), steps (618, 620, 622) may be repeated as described above (one or more times) to determine whether the measured firing motor temperature exceeds the maximum firing motor temperature threshold. In FIG. 17, between time (t0) and time (t5), there is no change between normal control operation (654) compared to motor control using firing motor temperature triggers (656).

At step (626), if the measured firing motor temperature exceeds the maximum firing motor temperature threshold as determined by motor controller (320), motor controller (320) stop power to motor (316). As shown in FIG. 17, after time (t5), motor (316) turns off once firing motor temperature (T2) is exceeded. Power may be reactivated to motor (316), in various manners (e.g., using steps (628, 630)). For example, at step (628), motor controller (320) may provide power to motor (316) after a predetermined period of time has elapsed or after the measured firing motor temperature is below a predetermined firing motor temperature threshold. As shown in FIG. 17, after time (t5), motor (316) turns off until firing motor temperature decreases to firing motor temperature (T1), where motor controller (320) instructs motor (316) to soft start as described above. At step (629), steps (618, 620) may be repeated as described above to repeatedly determine whether the measured firing motor temperature exceeds the maximum temperature threshold. The soft start of motor (316) continues until firing motor temperature (T2) is reached corresponding to a trigger limit (threshold) to prevent overheating (which occurs at time (t9)). At time (t9), motor (316) turns off once firing motor temperature (T2) is exceeded.

At step (630), motor controller (320) may calculate the change in firing motor temperature for based on the distance already traveled and extrapolate the estimated change in temperature for distance left to complete firing stroke to ensure the estimated change in temperature is below maximum firing motor temperature threshold. The firing stroke may be completed when the staples are each deployed from staple cartridge (156) or when firing assembly (158) reaches the distal most position. Motor controller (320) may calculate the change in temperature/based on distance traveled and estimated change in temperature for distance left to complete stroke is below maximum firing motor temperature threshold. Motor (316) is configured to reduce or stop power to motor (316) based on a change in temperature of motor (316) due to the distance traveled by driving assembly (164) relative to an estimated change in temperature of motor (316) due to the distance still to travel for driving assembly (164) to complete the firing sequence. In other words, motor controller (320) calculates the change in temperature increase over the distance traveled thus far and estimates the expected temperature increase for the distance left to travel and remains off until it could complete the full firing stroke. For example, a greater expected temperature increase results in a longer waiting period where motor (316) remains off. As shown in FIG. 17, motor (316) turns off between time (t9) and time (t10), which allows for driving assembly (164) to complete the full firing stroke before motor (316) turns back on.

At step (632), motor controller (320) activates motor (316) to complete the firing stroke based on the calculation determined in step (630). At step (634), steps (618, 620) may be repeated as described above one or more times to determine whether the measured firing motor temperature exceeds the maximum firing motor temperature threshold.

E. Motor Control Based on Lockout Status

Figure 18:
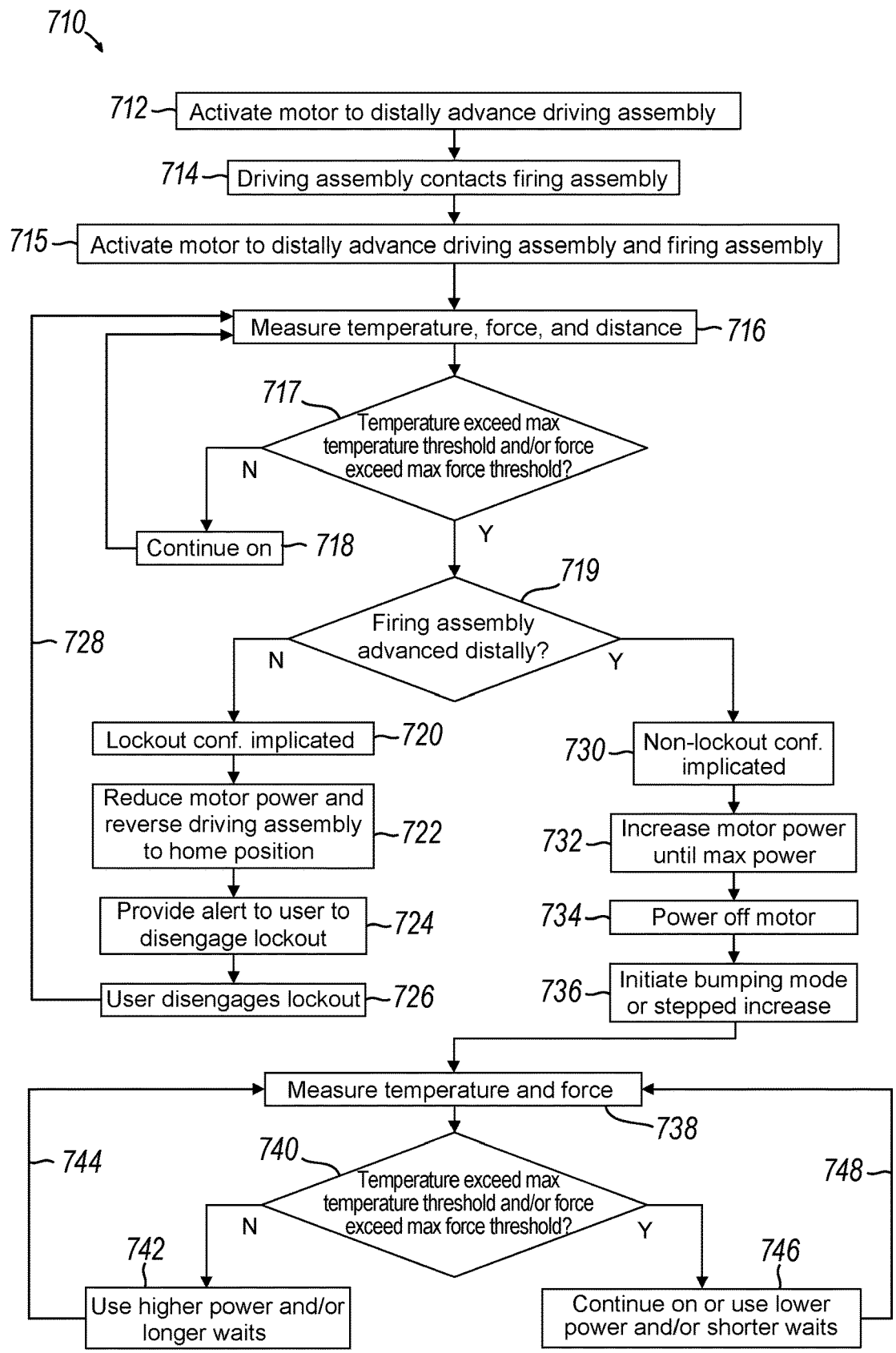
FIG. 18 depicts a block diagram of a fourth exemplary motor control algorithm that may be used by the robotic arm and surgical instrument shown in FIG. 12.
Figure 19A:
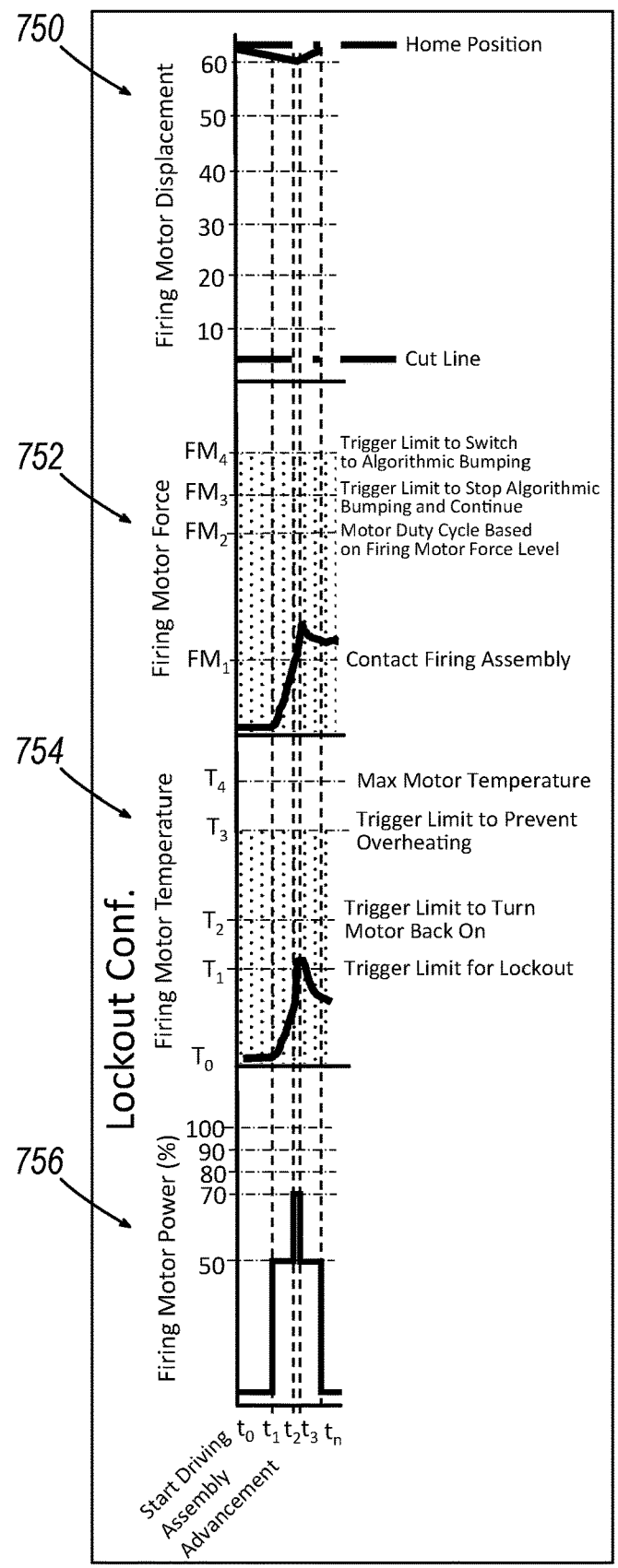
FIG. 19A depicts a multi-axis line graph with plots of firing motor displacement, firing motor force, firing motor temperature, and firing motor power with respect to time when a lockout assembly is in a lockout configuration for the exemplary method of FIG. 18.
Figure 19B:
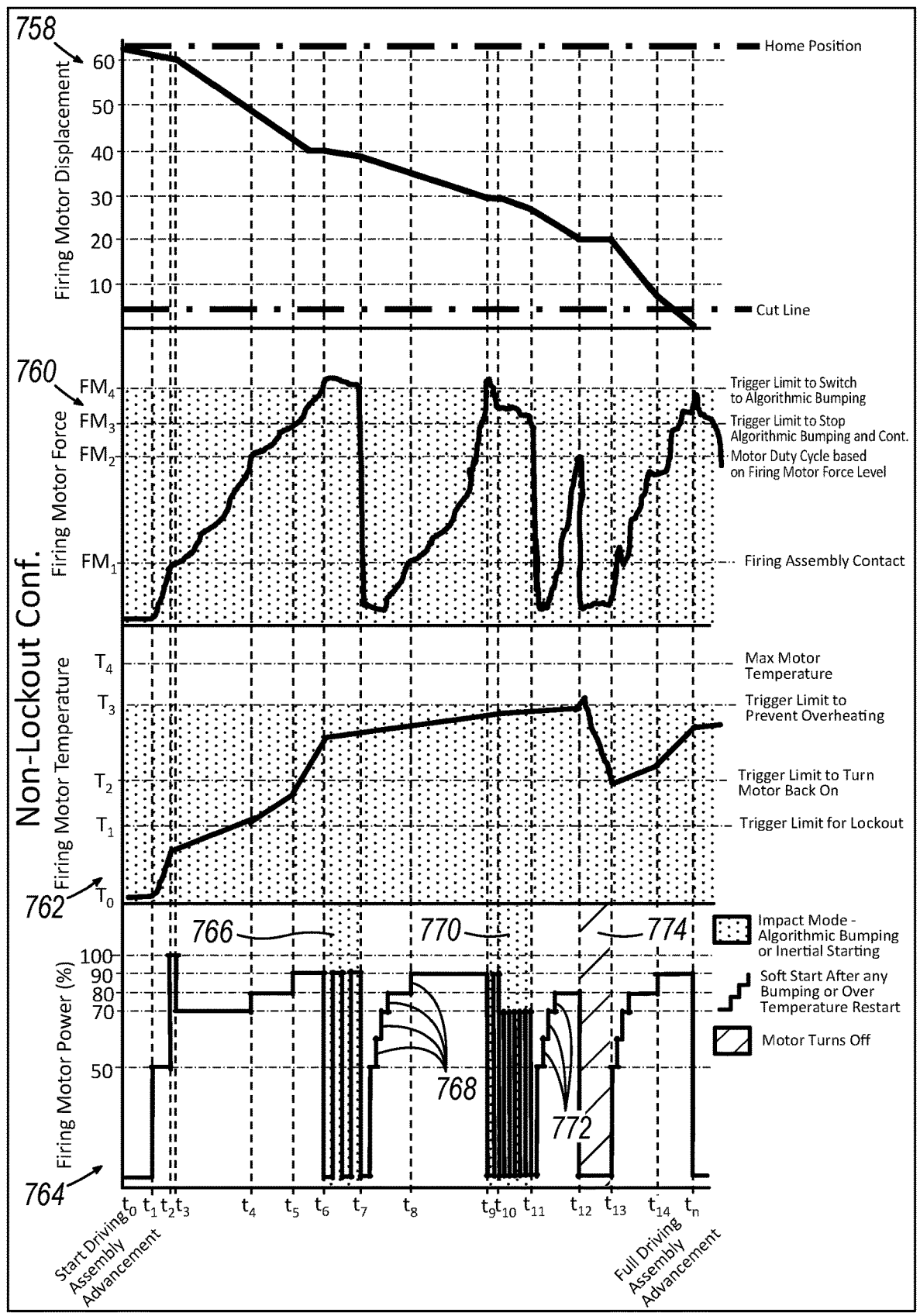
FIG. 19B depicts a multi-axis line graph with plots of firing motor displacement, firing motor force, firing motor temperature, and firing motor power with respect to time similar to FIG. 19A, but with the lockout assembly in a non-lockout configuration for the exemplary method of FIG. 18.

As described with reference to FIGS. 18-19B, method (710) includes exemplary steps (712, 714, 715, 716, 717, 718, 719, 720, 722, 724, 726, 728, 730, 732, 734, 736, 738, 740, 742, 744, 746, 748) which are described together with plots (750, 752, 754, 756, 758, 760, 762, 764) of FIGS. 19A-19B. While FIGS. 18-19B are described below with reference to the structures of FIGS. 1-9, method (710) may also be used with the structures of FIGS. 10-11. At step (712), motor controller (320) may activate motor (316) to distally advance driving assembly (164). At step (714), motor controller (320) may activate motor (316) so that driving assembly (164) contacts firing assembly (158), which is shown at time (t2) in plot (752) of FIG. 19A. FIG. 19 shows that at a predefined firing motor force limit that the firing motor temperature limit is hit indicating that the firing system made initial contact with wedge sled (170) of firing assembly (158).

At step (715), motor controller (320) may activate motor (316) to distally advance driving assembly (164) and firing assembly (158). At step (716), firing motor force, firing motor temperature, and/or distance may be measured. This firing motor force and firing motor temperature may be measured by motor controller (320) interpreting data produced by motor (316) during operation and/or through the use of a sensor assembly (318) operatively coupled with motor (316) and motor controller (320). In other words, sensor assembly (318) may measure at least one of a measured firing force of motor (316) or a measured firing motor temperature of motor (316) as motor (316) moves driving assembly (164). While not shown, sensor assembly (318) may include a position sensor may to determine if firing assembly (158) advances distally. In some versions, the position sensor is disposed in end effector (116, 210).

Step (717) may include determining whether the measured firing motor force exceeds the maximum firing motor force threshold and/or whether the measured firing motor temperature exceeds the maximum firing motor temperature threshold using motor controller (320). Threshold values may be stored in storage device (326) for retrieval by motor controller (320). At step (718), if the measured firing motor temperature exceeds the maximum firing motor temperature threshold and if the measured firing motor force does not exceed the maximum firing motor force threshold as determined by motor controller (320), motor (316) may continue on using a predetermined firing sequence until completion of the firing sequence. This measuring and determination may be repeated as described above (one or more times).

At step (719), if the measured firing motor temperature exceeds the maximum firing motor temperature and/or the measured firing motor force exceeds the maximum firing motor force threshold, motor controller (320) determines whether firing assembly is advanced distally. At step (720), if firing assembly (158) is not advanced distally, then the lockout mode implicated. As shown in plot (752) of FIG. 19A between time (t2) and time (t3), the firing motor temperature exceeds firing motor temperature (T1) which is the trigger limit for lockout assembly (314). As shown in plot (750) of FIG. 19A, firing motor displacement does not go below 60 millimeters (for a 60 mm staple cartridge), indicating firing assembly (158) is not advanced distally meaning that lockout assembly (314) is in the lockout configuration. At step (722), once motor controller (320) determines the lockout configuration is implicated, motor controller (320) may reduce/stop power of motor (316) and/or driving assembly (164) may be reversed to the home position. The lockout configuration does not allow the driving assembly (164) to advance once certain triggers are hit (e.g., firing motor temperature or firing motor force), and as driving assembly (164) continues to drive forward the firing motor force and firing motor temperature begin to increase since the lockout assembly (314) is not disengaged and motor (316) is trying to drive the system against itself. Motor (316) may proximally translate driving assembly (164) in response to motor controller (320) determining lockout assembly (314) is in the lockout configuration.

At step (724), an alert may be provided to the user to disengage lockout assembly (314). The alert may include one or more of a visual indication, a tactile indication, an audible indication. At step (726), the user may disengage lockout assembly (314) to switch lockout assembly (314) to the non-lockout configuration. After disengaging lockout assembly (314), step (716) may again be performed.

At step (730), if firing assembly (158) advances distally then the non-lockout configuration is implicated (since firing assembly (158) travels distally beyond the point where lockout assembly (314) prevents travel). As shown in plot (758) of FIG. 19B, firing motor displacement drops below 60 millimeters. At step (732), in response to determining the non-lockout configuration is implicated, motor controller (320) may increase power of motor (316). Motor (316) is configured to modify the motion profile by increasing power to motor (316) until a maximum firing motor force threshold of motor (316) is reached. Maximum firing motor power is reached at time (t2) in plot (764) of FIG. 19B. The non-lockout configuration proceeds forward if the firing motor distance, firing motor temperature, firing motor force limits are acceptable. As shown in FIG. 19B, the power of motor (316) increases as different firing motor force limits are hit allowing the motor (316) to step up until a maximum firing motor force threshold is hit.

At step (734), method (710) may include motor controller (320) ceasing power to motor (316). and response to the maximum firing motor force threshold of motor (316) being reached, powering off motor (316). Once the maximum firing motor force threshold is exceeded, motor controller (320) turns off motor (316). After powering off motor (316), restarting motor (316) after one of a predetermined time, a predetermined temperature, or an estimated temperature to deploy staples from staple cartridge (154, 218). At step (736), motor controller (320) may initiate algorithmic bumping mode (at time (t6) in plot (764) of FIG. 19B). At step (740), motor controller (320) determines whether the measured firing motor temperature exceeds max temperature threshold and/or whether the measured firing motor force exceed maximum firing motor force threshold. At step (738), if measured firing motor temperature does not exceed max temperature threshold and the measured firing motor force does not exceed the maximum firing motor force threshold motor controller (320) may instruct motor (316) to use higher power and/or longer waits (shown by soft start (768)). At step (740), if measured firing motor temperature exceeds max temperature threshold and/or the measured firing motor force exceeds the maximum firing motor force threshold, motor controller (320) may instruct motor (316) to continue on or use lower power and/or shorter waits.

In some versions, motor controller (320) may modify the motion profile by alternating cycle rate or changing the speed at which driving assembly (164) travels. The response of the impact/bumping mode depends on the response of the firing motor force of plot (760) and firing motor temperature of plot (762). As shown in plot (760), a first impact/bumping mode (766) (shown in plot (764) using stippling) continues with higher power and longer pauses/cycles since the measured firing motor force did not reduce. Once the firing motor force decreases below the tolerable trigger limit and temperature limit is tolerable, driving assembly (164) re-engages in a soft start mode for a defined set point then return to a variable motor power level based on predefined inputs. Motor (316) turns off for a predetermined time or temperature, a soft start may be used to turn motor (316) on at a lower state than originally reduce the likelihood of overheating motor (316) to overheat or slowly turn motor (316) on to be able to check parameters before returning to a normal state.

The second impact/bumping mode (770) (shown in plot (764) using stippling) initially starts with a high-power cycle and the firing motor force drops in which the response is the lower power quicker impacts/bumping until it hits the trigger limit to continue operation. As shown, once the firing motor temperature trigger (T3) is hit at time (t12), then power to motor (316) is cycled off until the firing motor temperature trigger (T2) is met in which driving assembly (164) re-engages firing assembly (158) and continues to drive forward until completion of the firing stroke. Cooperative or interrelated triggers may act upon each other to drive or change the response during a cycle. The cooperative or interrelated trigger optimize responses. Interrelated triggers (e.g., using both motor firing force and motor firing temperature) may change the response of the firing system. The cycle has alternative (or different response) after triggers were hit.

As shown in plot (764) of FIG. 19, motor controller (320) is configured to reduce or stop power to motor (316) for a predetermined period of time (e.g., between time (t12) and time (t13)) in response to either the firing motor force exceeding the predetermined firing motor force threshold or the temperature exceeding the predetermined firing motor temperature threshold. This waiting period (774) is shown in plot (764) using a hashed pattern. The waiting period (774) is where motor (316) turns off once firing motor temperature (T3) is exceeded, and the time off duration may be based on distance required to meet full travel and the delta temperature increase based on completed stroke.

F. Motor Control Using Voltage Modulation and/or Efficiency

Figure 20:
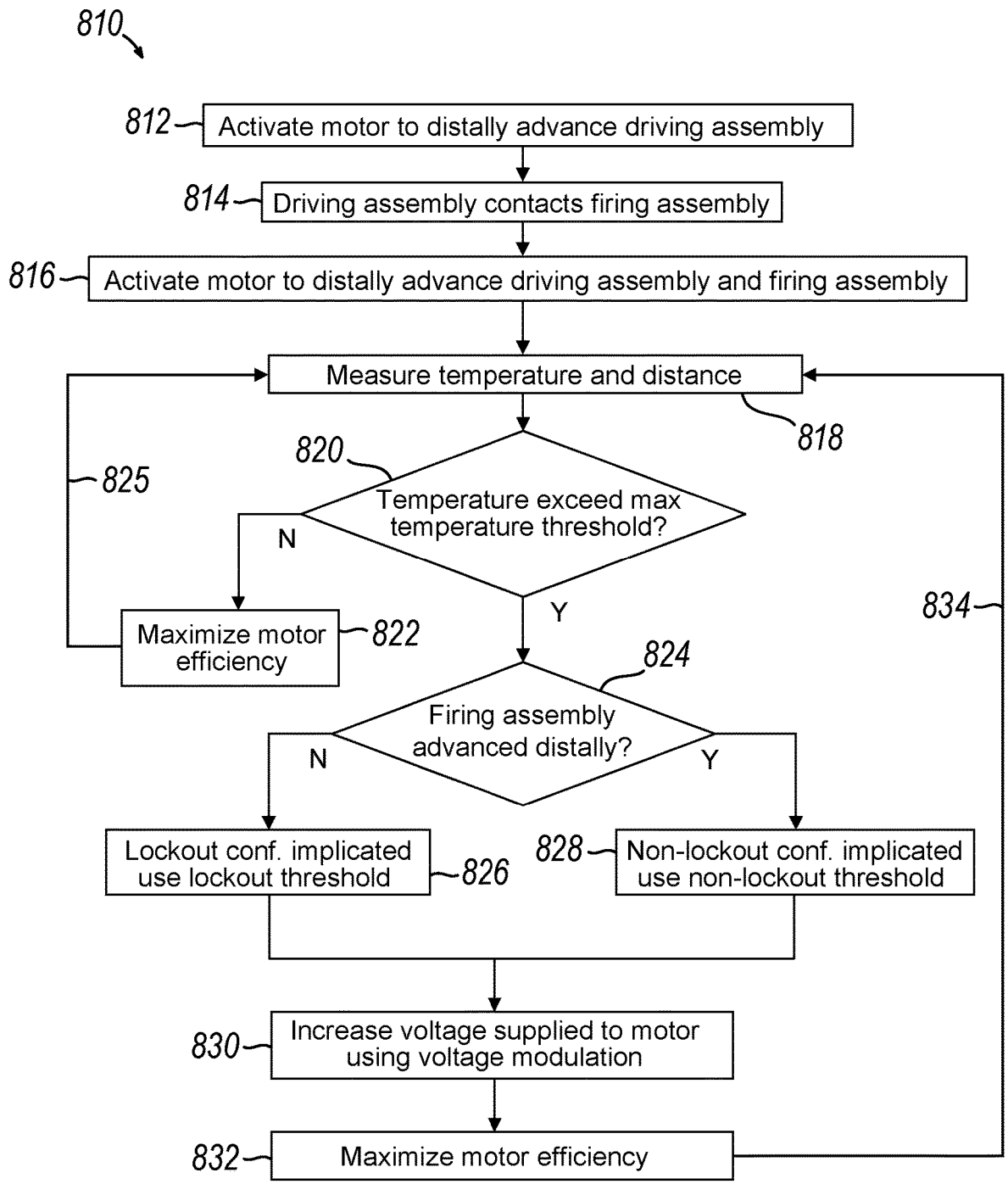
FIG. 20 depicts a block diagram of a fifth exemplary motor control algorithm that may be used by the robotic arm and surgical instrument shown in FIG. 12.
Figure 21A:
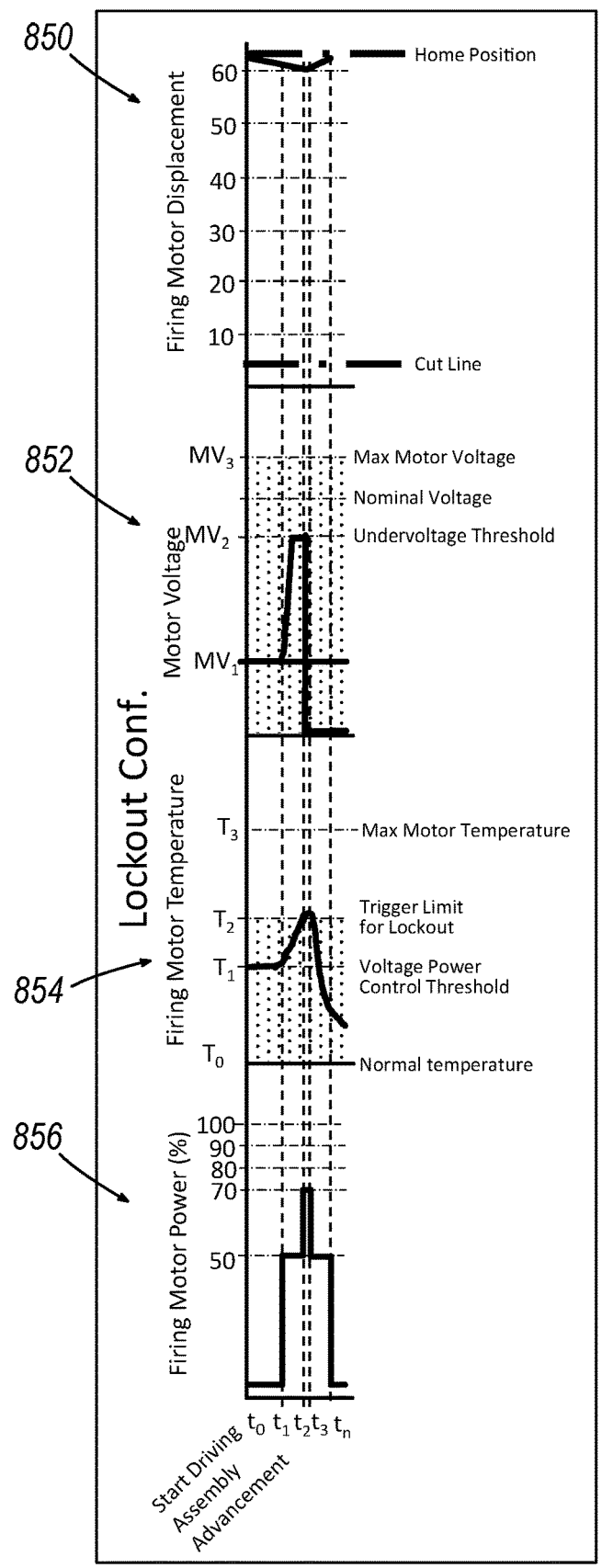
FIG. 21A depicts a multi-axis line graph with plots of firing motor displacement, motor voltage, firing motor temperature, and firing motor power with respect to time when a lockout assembly is in a lockout configuration for the exemplary method of FIG. 20.
Figure 21B:
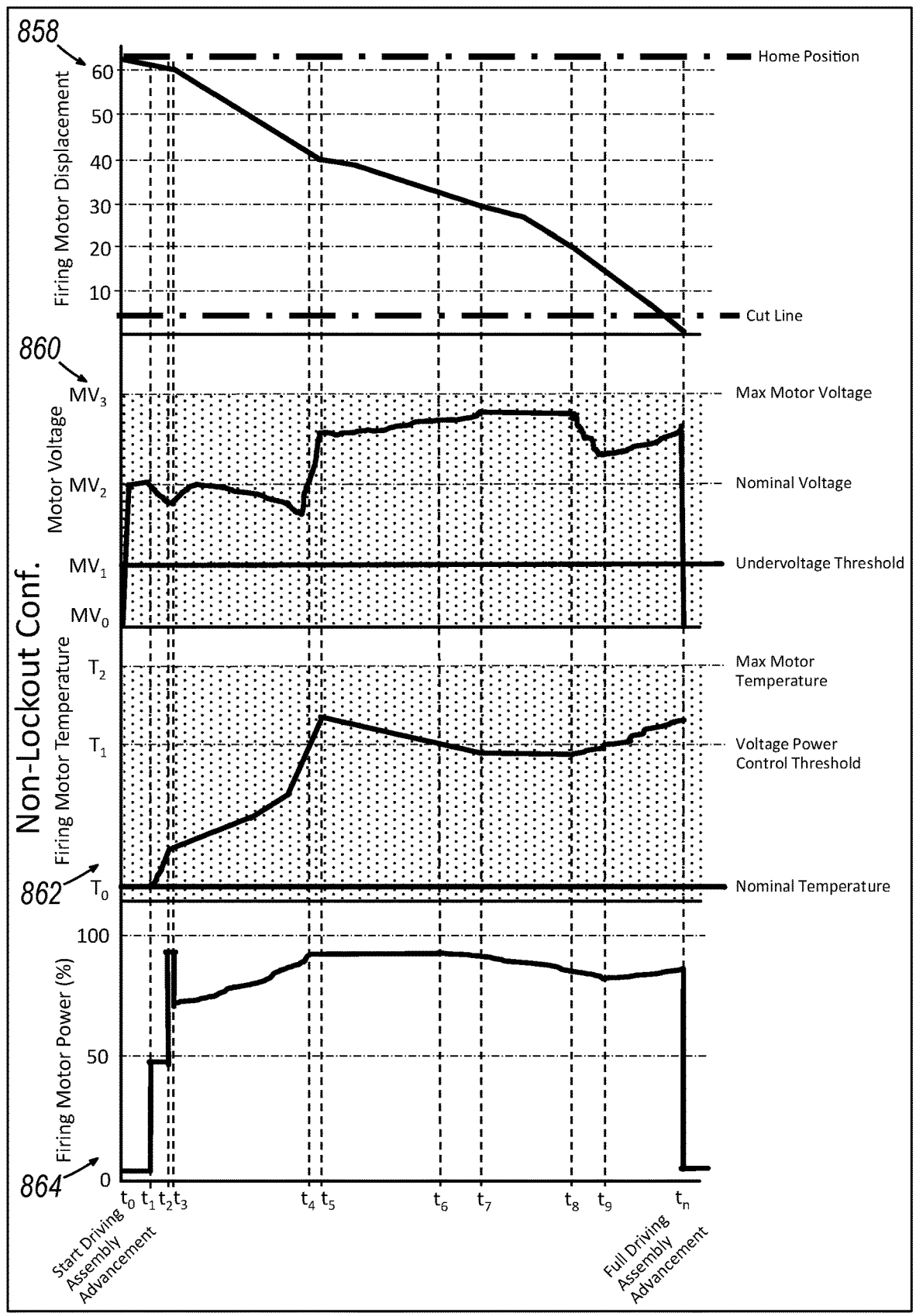
FIG. 21B depicts a multi-axis line graph with plots of firing motor displacement, motor voltage, firing motor temperature, and firing motor power with respect to time similar to FIG. 21A, but with the lockout assembly in a non-lockout configuration for the exemplary method of FIG. 20.
Figure 22:
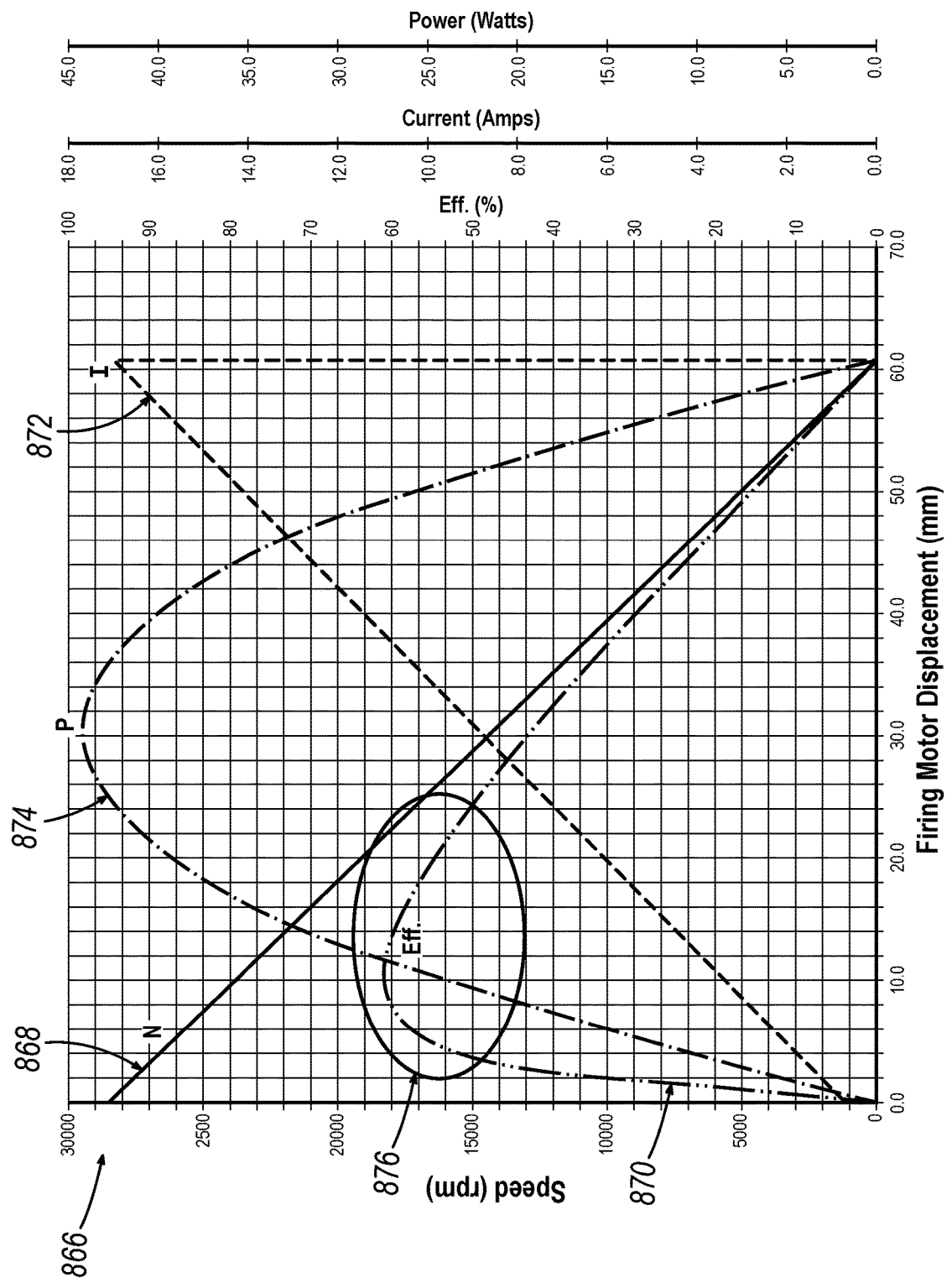
FIG. 22 depicts a multi-line graph with overlying plots of speed, efficiency, current, and power with respect to firing motor displacement for the exemplary method of FIG. 20.

As described with reference to FIGS. 20-22, method (810) includes exemplary steps (812, 814, 816, 818, 820, 822, 824, 825, 826, 828, 830, 832, 834), which is described together with plots (850, 852, 854, 856) of FIG. 21A, plots (858, 860, 862, 864) of FIG. 21B, and plots (868, 870, 872, 874) of FIG. 22. While FIGS. 20-22 are described below with reference to the structures of FIGS. 1-9, method (810) may also be used with the structures of FIGS. 10-11.

At step (812), motor controller (320) may activate motor (316) to distally advance driving assembly (164). At step (814), motor controller (320) may activate motor (316) so that driving assembly (164) contacts firing assembly (158). At step (816), motor controller (320) may activate motor (316) to distally advance driving assembly (164) and firing assembly (158). At step (818), temperature and distance may be measured. This temperature may be measured by motor controller (320) interpreting data produced by motor (316) during operation and/or through the use of a sensor assembly (318) operatively coupled with motor (316) and motor controller (320). Similar to step (716), step (818) may also include measuring distance.

At step (820), motor controller (320) may determine whether the measured firing motor temperature exceeds the maximum firing motor temperature threshold. The firing motor temperature thresholds may be stored in storage device (326) for retrieval by motor controller (320) to determine if firing assembly (158) moves distally similar to step (719). At step (822), if the measured firing motor temperature does not exceed the maximum firing motor temperature threshold as determined by motor controller (320), motor controller (320) may optimize efficiency of motor (316). Motor controller (320) adjusts performance of motor (316) to maximize the efficiency of motor (316) and regulate the thermal load. At least one control parameter of motor (316) may be modified based on the sensed values of interrelated triggers to maximize the efficiency curve of motor (316). At step (825), steps (818, 820, 822) may be repeated as described above (one or more times) to determine whether the measured firing motor temperature exceeds the maximum firing motor temperature threshold.

At step (824), and similar to step (719), if the measured firing motor temperature exceeds the maximum temperature threshold as determined by motor controller (320), motor controller (320) may determine if firing assembly (158) is in the lockout configuration or the non-lockout configuration based on distance traveled. In the lockout configuration, as shown at time (t2) in plot (854) of FIG. 21A, motor (316) turns off once firing motor temperature (T2) is exceeded. Additionally, in plot (852), motor voltage does not exceed motor voltage (MV2) which is the undervoltage threshold. As shown in plot (850) of FIG. 21A, firing motor displacement does not go below 60 millimeters, indicating firing assembly (158) is not advanced distally indicating lockout assembly (314) is in the lockout configuration.

At step (826) if the measured temperature exceeds the maximum firing motor temperature, motor controller (320) determines whether firing assembly (158) is advanced distally. At step (720), if firing assembly (158) is not advanced distally, then the lockout configuration is implicated. In FIGS. 21A-21B, time (t0) refers to the time when driving assembly (164) starts being advanced, while time (tn) refers to the time when driving assembly (164) is fully advanced. The stippling shaded region depicted of plots (852, 860) of FIGS. 21A-21B represent a tolerable range of firing motor force, and the stippling shaded region depicted of plots (854, 862) represent a tolerable range of firing motor temperature threshold for driving assembly (164).

At step (828), if firing assembly (158) advances distally then the non-lockout configuration is implicated (since firing assembly (158) travels distally beyond the point where lockout assembly (314) prevents travel). As shown in plot (858) of FIG. 21B, firing motor displacement drops below 60 millimeters. At step (830), increasing the firing motor voltage supplied to motor (316) using voltage modulation. Where one of the interrelated triggers includes the measured firing motor temperature exceeding the maximum firing motor temperature threshold of motor (316), the firing motor voltage supplied to motor (316) is increased in response to motor (316) reaching the predetermined firing motor temperature threshold. In response to the firing motor voltage supplied to motor (316) being increased, the speed of motor (316) is increased. Motor controller (320) is configured to modify the motion profile by instructing motor (316) to provide continuous power to alter performance of end effector (116, 210).

DC motors follow a defined performance curve for their performance. Motor heating is associated with current through the windings. From Ohm's law, the energy loss to heat is the current squared times the windings resistance $I^2R$. Power to the motor is defined by Power=Voltage×Current. When motor (316) begins to experience a thermal event, motor (316) responds by increasing the voltage supplied to motor (316). By increasing the voltage supplied to motor (316), the required current decreases, and the power remains the same, thus lowering the $I^2R$ in the motor windings. Due to the motor curve, the increase in voltage increases the speed of motor (316). This characteristic may be mitigated using pulse width modulation to affect the signal powering motor (316) to lower the overall power utilized by motor (316). At step (832), efficiency of motor (316) may be maximized as described above with reference to step (822).

FIG. 22 shows a graph (866) of plots (868, 870, 872, 874). Plot (868) refers to the distance travelled for firing assembly (158), shown as firing motor displacement in millimeters. Plot (868) shows motor speed linearly decreasing as the firing displacement decreases. Plot (870) shows firing motor efficiency at a maximum of over 60% at a firing motor displacement of approximately 10 millimeters. Plot (872) shows current linearly increasing. Plot (874) shows a parabolic curve of power reaching a maximum at approximately a firing motor displacement of approximately 30 millimeters. The encircled region (876) is where efficiency is maximized. In some versions, motor controller (320) instructs motor (316) to operate in the encircled region (876) to maximize the cumulative benefits through assessing multiple trigger variables in combination. For example, encircled region (876) may use data from plots (868, 870, 872, 874).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft assembly extending distally; (b) an end effector operatively coupled with the shaft assembly, wherein the end effector comprises: (i) a first jaw including an anvil, and (ii) a second jaw including a stapling assembly having staples; (c) a driving assembly; (d) at least one motor configured to actuate the driving assembly to deploy the staples from the stapling assembly; and (e) a motor controller in communication with the motor and configured to: (i) determine whether values of first and second trigger variables exceed predetermined thresholds, and (ii) in response to determining that the values of the first and second trigger variables exceed the predetermined thresholds, modify at least one motor control parameter of the following motor control parameters: (A) a motion profile instituted by the motor controller for the motor, (B) a waiting period during which power to the motor is reduced or stopped, or (C) the predetermined threshold relating to current or force for proximal retraction of the driving assembly to be different from the predetermined threshold relating to current or force for distal advancement of the driving assembly.

Example 2

The surgical instrument of Example 1, wherein the motor controller is configured to withhold modification of the at least one control parameter until each of the values of the first and second trigger variables exceed the predetermined thresholds

Example 3

The surgical instrument of Example 1, wherein the motor controller is configured to modify the at least one control parameter differently in response to each of the values of the first and second trigger variables exceeding the predetermined thresholds as compared to a single of the one the first and second trigger variables exceeding the respective predetermined threshold.

Example 4

The surgical instrument of Example 1, further comprising a sensor assembly configured to sense the values of the first and second trigger variables and communicate the values to the motor controller.

Example 5

The surgical instrument of any one or more of the preceding Examples, wherein in response to the values exceeding the predetermined thresholds, the motor controller is configured to modify at least two of the motor control parameters.

Example 6

The surgical instrument of any one or more of the preceding Examples, wherein one of the first or second trigger variables comprises: (A) a measured force of the motor, (B) a measured temperature of the motor, (C) a measured current supplied to the motor, (D) a measured voltage supplied to the motor, or (E) a measured distance associated with a lockout assembly of the surgical instrument, wherein the measured distance is indicative of the lockout assembly being in a lockout configuration or a non-lockout configuration.

Example 7

The surgical instrument of any one or more of the preceding Examples, wherein the at least one motor control parameter comprises a motion profile of the motor, wherein the motor controller is configured to: (A) modify the motion profile by increasing motor power until a predetermined force threshold of the motor is reached, and (B) in response to the predetermined force threshold of the motor being reached, power off the motor.

Example 8

The surgical instrument of Example 7, wherein after powering off the motor, the motor controller is configured to restart the motor after one of a predetermined time or a predetermined temperature.

Example 9

The surgical instrument of any one or more of the preceding Examples, wherein the first trigger variable comprises a measured temperature of the motor, wherein the second trigger variable comprises a voltage supplied to the motor, wherein the motor controller is configured to increase the voltage in response to the measured temperature reaching a predetermined temperature threshold.

Example 10

The surgical instrument of any one or more of the preceding Examples, further comprising a lockout assembly configured to assume a lockout configuration to prevent actuation of the end effector, wherein the motor controller is configured proximally translate the driving assembly in response to the motor controller determining the lockout assembly is in the lockout configuration.

Example 11

The surgical instrument of any one or more of Examples 1 through 9, wherein the first and second trigger variables comprise two of: (A) a measured force of the motor, (B) a measured temperature of the motor, (C) a measured current supplied to the motor, (D) a measured voltage supplied to the motor, and (E) a measured distance associated with a lockout assembly of the surgical instrument, wherein the measured distance is indicative of the lockout assembly being in a lockout configuration or a non-lockout configuration.

Example 12

The surgical instrument of any one or more of the preceding Examples, wherein by modifying the at least one motor control parameter of the motor controller based on the values of the first and second trigger variables, the motor controller is configured to maximize an efficiency of the motor.

Example 13

The surgical instrument of any one or more of the preceding Examples, wherein the motor controller is configured to reduce or stop power to the motor in response to identifying a difference between a sensed change in temperature of the motor due to actuation of the driving assembly and an estimated change in temperature of the motor due to actuation of the driving assembly to deploy the staples from the stapling assembly.

Example 14

The surgical instrument of any one or more of the preceding Examples, wherein the at least one motor control parameter comprises a motion profile of the motor, wherein the motor controller is configured to modify the motion profile by alternating cycle rate or changing the speed at which the driving assembly travels.

Example 15

The surgical instrument of any one or more of the preceding Examples, wherein the at least one motor control parameter comprises a motion profile of the motor, wherein the motor controller is configured to modify the motion profile by instructing the motor to provide an intermittent pulse of power or continuous power to alter performance of the end effector.

Example 16

The surgical instrument of any one or more of the preceding Examples, wherein the driving assembly extends through at least a portion of the shaft assembly and the end effector, wherein the driving assembly is operable to staple and cut tissue based on instruction from the motor controller.

Example 17

A robotic surgical system comprising: (a) a robotic arm; and (b) the surgical instrument of any one or more of the preceding Examples, wherein the surgical instrument is configured to removably couple with the robotic arm.

Example 18

A surgical instrument comprising: (a) a shaft assembly extending distally; (b) an end effector operatively coupled with the shaft assembly, wherein the end effector comprises: (i) a first jaw including an anvil, and (ii) a second jaw including a stapling assembly having staples, wherein at least one of the first or second jaws is configured to pivot relative to the other of the first or second jaws between an open position and a closed position; (c) a driving assembly; (d) a motor configured to actuate the driving assembly to deploy the staples; (e) a sensor assembly configured to measure at least one of a firing force of the motor or a temperature of the motor as the motor actuates the driving assembly; and (f) a motor controller in communication with the motor and configured to: (i) determine at least one of whether the measured firing force of the motor exceeds a predetermined force threshold or whether the measured temperature of the motor exceeds a predetermined temperature threshold, and (ii) reduce or stop power to the motor in response to determining that the measured firing force exceeds the predetermined force threshold or the measured temperature exceeds the predetermined temperature threshold.

Example 19

The surgical instrument of Example 18, wherein the motor controller is configured to reduce or stop power to the motor for a predetermined period of time in response to determining that the measured firing force exceeds the predetermined force threshold or the measured temperature exceeds the predetermined temperature threshold.

Example 20

The surgical instrument of any one or more of Examples 18 through 19, wherein the motor controller is configured to reduce or stop power to the motor in response to identifying a difference between a sensed change in temperature of the motor due to actuation of the driving assembly and an estimated change in temperature of the motor due to actuation of the driving assembly to deploy the staples from the stapling assembly.

Example 21

The surgical instrument of any one or more of Examples 16 through 17, wherein the motor controller is further configured to repeatedly start and stop the motor until at least one of the measured firing force is less than a second force threshold or the measured temperature is less than a second temperature threshold.

Example 22

A method of firing a robotically controlled end effector with a motor and a driving assembly to at least one of staple or cut tissue with the end effector, the method comprising: (a) distally advancing the driving assembly within the end effector; (b) detecting values of first and second trigger variables; (c) in response to detecting the values, determining whether the values exceed predetermined thresholds; and (d) in response to determining that the values of the first and second trigger variables exceed the predetermined thresholds, modifying at least one of: (i) a motion profile instituted by the motor controller for the motor, (ii) a waiting period during which power to the motor is reduced or stopped, or (iii) the predetermined threshold relating to current or force for proximal retraction of the driving assembly to be different from the predetermined threshold relating to current or force for distal advancement of the driving assembly.

IV. MISCELLANEOUS

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,677, entitled "Variable Response Motor Control Algorithm for Powered Surgical Stapler," filed on Aug. 16, 2021, published as U.S. Pub. No. 2023/0048444 on Feb. 16, 2023; U.S. patent application Ser. No. 17/402,679, entitled "Powered Surgical Stapler Having Independently Operable Closure and Firing Systems," filed on Aug. 16, 2021, published as U.S. Pub. No. 2023/0051756 on Feb. 16, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701 entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703 entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Sled Restraining Member for Surgical Stapler," filed on Aug. 16, 2021, published as U.S. Pub. No. 2023/0045893 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a shaft assembly extending distally;
   (b) an end effector operatively coupled with the shaft assembly, wherein the end effector comprises:
      (i) a first jaw including an anvil, and
      (ii) a second jaw including a stapling assembly having staples;
   (c) a driving assembly;
   (d) at least one motor configured to actuate the driving assembly to deploy the staples from the stapling assembly; and
   (e) a motor controller in communication with the motor and configured to:
      (i) determine whether values of first and second trigger variables exceed predetermined thresholds, and
      (ii) in response to determining that the values of the first and second trigger variables exceed the predetermined thresholds, modify at least one motor control parameter of the following motor control parameters:
         (A) a motion profile instituted by the motor controller for the motor,
         (B) a waiting period during which power to the motor is reduced or stopped, or
         (C) the predetermined threshold relating to current or force for proximal retraction of the driving assembly to be different from the predetermined threshold relating to current or force for distal advancement of the driving assembly.

2. The surgical instrument of claim 1, wherein the motor controller is configured to withhold modification of the at least one control parameter until each of the values of the first and second trigger variables exceed the predetermined thresholds.

3. The surgical instrument of claim 1, wherein the motor controller is configured to modify the at least one control parameter differently in response to each of the values of the first and second trigger variables exceeding the predetermined thresholds as compared to a single of the one the first and second trigger variables exceeding the respective predetermined threshold.

4. The surgical instrument of claim 1, further comprising a sensor assembly configured to sense the values of the first and second trigger variables and communicate the values to the motor controller.

5. The surgical instrument of claim 1, wherein in response to the values exceeding the predetermined thresholds, the motor controller is configured to modify at least two of the motor control parameters.

6. The surgical instrument of claim 1, wherein one of the first or second trigger variables comprises:
   (A) a measured force of the motor,
   (B) a measured temperature of the motor,
   (C) a measured current supplied to the motor,
   (D) a measured voltage supplied to the motor, or
   (E) a measured distance associated with a lockout assembly of the surgical instrument, wherein the measured distance is indicative of the lockout assembly being in a lockout configuration or a non-lockout configuration.

7. The surgical instrument of claim 1, wherein the at least one motor control parameter comprises a motion profile of the motor, wherein the motor controller is configured to:
   (A) modify the motion profile by increasing motor power until a predetermined force threshold of the motor is reached, and
   (B) in response to the predetermined force threshold of the motor being reached, power off the motor.

8. The surgical instrument of claim 1, wherein the first trigger variable comprises a measured temperature of the motor, wherein the second trigger variable comprises a voltage supplied to the motor, wherein the motor controller is configured to increase the voltage in response to the measured temperature reaching a predetermined temperature threshold.

9. The surgical instrument of claim 1, further comprising a lockout assembly configured to assume a lockout configuration to prevent actuation of the end effector, wherein the motor controller is configured proximally translate the driving assembly in response to the motor controller determining the lockout assembly is in the lockout configuration.

10. The surgical instrument of claim 1, wherein the first and second trigger variables comprise two of:
    (A) a measured force of the motor,
    (B) a measured temperature of the motor,
    (C) a measured current supplied to the motor,
    (D) a measured voltage supplied to the motor, and
    (E) a measured distance associated with a lockout assembly of the surgical instrument, wherein the measured distance is indicative of a lockout assembly being in a lockout configuration or a non-lockout configuration.

11. The surgical instrument of claim 1, wherein by modifying the at least one motor control parameter of the motor controller based on the values of the first and second trigger variables, the motor controller is configured to maximize an efficiency of the motor.

12. The surgical instrument of claim 1, wherein the motor controller is configured to reduce or stop power to the motor in response to identifying a difference between a sensed change in temperature of the motor due to actuation of the driving assembly and an estimated change in temperature of the motor due to actuation of the driving assembly to deploy the staples from the stapling assembly.

13. The surgical instrument of claim 1, wherein the at least one motor control parameter comprises a motion profile of the motor, wherein the motor controller is configured to modify the motion profile by alternating cycle rate or changing the speed at which the driving assembly travels.

14. The surgical instrument of claim 1, wherein the at least one motor control parameter comprises a motion profile of the motor, wherein the motor controller is configured to modify the motion profile by instructing the motor to provide an intermittent pulse of power or continuous power to alter performance of the end effector.

15. A robotic surgical system comprising:
    (a) a robotic arm; and
    (b) the surgical instrument of claim 1, wherein the surgical instrument is configured to removably couple with the robotic arm.

16. A surgical instrument comprising:
    (a) a shaft assembly extending distally;
    (b) an end effector operatively coupled with the shaft assembly, wherein the end effector comprises:
       (i) a first jaw including an anvil, and
       (ii) a second jaw including a stapling assembly having staples, wherein at least one of the first or second jaws is configured to pivot relative to the other of the first or second jaws between an open position and a closed position;
    (c) a driving assembly;

(d) a motor configured to actuate the driving assembly to deploy the staples;

(e) a sensor assembly configured to measure at least one of a firing force of the motor or a temperature of the motor as the motor actuates the driving assembly; and a motor controller in communication with the motor and configured to:
  (i) determine at least one of whether the measured firing force of the motor exceeds a first predetermined force threshold or whether the measured temperature of the motor exceeds a first predetermined temperature threshold in response to the stapling assembly interacting with tissue,
  (ii) reduce or stop power to the motor using a first power profile in response to determining that the measured firing force exceeds the first predetermined force threshold or the measured temperature exceeds the first predetermined temperature threshold,
  (iii) after reducing or stopping power to the motor, determine at least one of whether the measured firing force of the motor exceeds a second predetermined force threshold or whether the measured temperature of the motor exceeds a second predetermined temperature threshold in response to the stapling assembly interacting with tissue, wherein the second predetermined force threshold is greater than the first predetermined force threshold, wherein the second predetermined temperature threshold is greater than the first predetermined temperature threshold, and
  (iv) reduce or stop power to the motor using a second power profile that is different than the first power profile in response to determining that the measured firing force exceeds the second predetermined force threshold or the measured temperature exceeds the second predetermined temperature threshold.

17. The surgical instrument of claim 16, wherein the motor controller is configured to reduce or stop power to the motor for a predetermined period of time in response to determining that the measured firing force exceeds the second predetermined force threshold or the measured temperature exceeds the second predetermined temperature threshold.

18. The surgical instrument of claim 16, wherein the motor controller is configured to reduce or stop power to the motor in response to identifying a difference between a sensed change in temperature of the motor due to actuation of the driving assembly and an estimated change in temperature of the motor due to actuation of the driving assembly to deploy the staples from the stapling assembly to the tissue.

19. The surgical instrument of claim 16, wherein the motor controller is further configured to repeatedly start and stop the motor until at least one of the measured firing force is less than a third force threshold or the measured temperature is less than a third temperature threshold.

20. A method of firing a robotically controlled end effector with a motor and a driving assembly to at least one of staple or cut tissue with the end effector, the method comprising:
  (a) distally advancing the driving assembly within the end effector;
  (b) detecting values of first and second trigger variables;
  (c) in response to detecting the values, determining whether the values exceed predetermined thresholds; and
  (d) in response to determining that the values of the first and second trigger variables exceed the predetermined thresholds, modifying at least one of:
    (i) a motion profile instituted by the motor controller for the motor,
    (ii) a waiting period during which power to the motor is reduced or stopped, or
    (iii) the predetermined threshold relating to current or force for proximal retraction of the driving assembly to be different from the predetermined threshold relating to current or force for distal advancement of the driving assembly.

\* \* \* \* \*